(12) United States Patent
Clarke et al.

(10) Patent No.: US 6,951,732 B2
(45) Date of Patent: Oct. 4, 2005

(54) VIRULENCE GENES, PROTEINS, AND THEIR USE

(75) Inventors: Enda Elizabeth Clarke, Berkshire (GB); Liqing Zhou, Berkshire (GB); Jacqueline Elizabeth Shea, Berkshire (GB); Robert Graham Feldman, Berkshire (GB); David William Holden, Berkshire (GB)

(73) Assignee: VMAX Ltd. (GB)

( * ) Notice: Subject to any disclaimer, the term of this patent is extended or adjusted under 35 U.S.C. 154(b) by 0 days.

(21) Appl. No.: 10/169,048

(22) PCT Filed: Dec. 22, 2000

(86) PCT No.: PCT/GB00/04997

§ 371 (c)(1), (2), (4) Date: Sep. 23, 2002

(87) PCT Pub. No.: WO01/48208

PCT Pub. Date: Jul. 5, 2001

(65) Prior Publication Data

US 2003/0072769 A1 Apr. 17, 2003

(30) Foreign Application Priority Data

| Dec. 23, 1999 | (GB) | 9930462 |
|---|---|---|
| Dec. 23, 1999 | (GB) | 9930463 |
| Dec. 23, 1999 | (GB) | 9930464 |
| Dec. 23, 1999 | (GB) | 9930466 |
| Dec. 23, 1999 | (GB) | 9930467 |
| Dec. 23, 1999 | (GB) | 9930469 |
| Dec. 23, 1999 | (GB) | 9930471 |
| Dec. 23, 1999 | (GB) | 9930472 |
| Dec. 23, 1999 | (GB) | 9930473 |
| Dec. 23, 1999 | (GB) | 9930474 |
| Dec. 23, 1999 | (GB) | 9930475 |
| Dec. 23, 1999 | (GB) | 9930476 |
| Feb. 17, 2000 | (GB) | 0003725 |
| Feb. 17, 2000 | (GB) | 0003726 |
| Feb. 17, 2000 | (GB) | 0003727 |
| Feb. 17, 2000 | (GB) | 0003728 |
| Feb. 17, 2000 | (GB) | 0003729 |
| Feb. 17, 2000 | (GB) | 0003730 |
| Feb. 17, 2000 | (GB) | 0003731 |
| Feb. 17, 2000 | (GB) | 0003732 |
| Feb. 17, 2000 | (GB) | 0003733 |
| Feb. 17, 2000 | (GB) | 0003735 |
| Feb. 17, 2000 | (GB) | 0003736 |
| May 2, 2000 | (GB) | 0010585 |
| May 2, 2000 | (GB) | 0010587 |

(51) Int. Cl.$^7$ .......... C12Q 1/18; C12Q 1/70; C12Q 1/68; C07H 21/04

(52) U.S. Cl. .......... 435/32; 435/4; 435/5; 435/6; 435/69.1; 435/252.3; 435/320.1; 536/23.1; 536/23.7; 536/24.32; 424/243.1

(58) Field of Search .......... 435/4, 32, 5, 6, 435/69.1, 252.3, 320.1; 536/23.1, 23.7, 24.32; 424/243.1

(56) References Cited

FOREIGN PATENT DOCUMENTS

| EP | 0 786 519 A1 | 7/1997 |
| WO | WO 97/13786 A | 4/1997 |

OTHER PUBLICATIONS

Burgess et al., The Journal of Cell Biology, 111:2129–2138, 1990.*

Wessels, M.R. & M.S. Bronze (Dec. 6, 1994) "Critical role of the group A streptococcal capsule in pharyngeal colonization and infection in mice" *Proceedings of the National Academy of Sciences of USA* 91(25):12238–12242.

Ferretti, J.J. et al. (Apr. 10, 2001) "Complete genome sequence of an M1 strain of *Streptococcus pyogenes*" *Proceedings of the National Academy of Sciences of USA* 98(8):4658–4663.

* cited by examiner

*Primary Examiner*—L. F. Smith
*Assistant Examiner*—Padma Baskar
(74) *Attorney, Agent, or Firm*—Saliwanchik, Lloyd & Saliwanchik

(57) ABSTRACT

A series of genes from *Streptococcus pyogenes* are shown to encode products which are implicated in virulence. The identification of these genes therefore allows attenuated microorganisms to be produced. Furthermore, the genes or their encoded products can be used in the manufacture of vaccines for therapeutic application.

1 Claim, No Drawings

SEQUENCE LISTING

<160> NUMBER OF SEQ ID NOS: 62

<210> SEQ ID NO 1
<211> LENGTH: 666
<212> TYPE: DNA
<213> ORGANISM: Streptococcus pyogenes

<400> SEQUENCE: 1

```
atggatcaaa ccattcatca ccaaatacag caagcactac actttagaac agccgttcgt    60
gtttataagg aagaaaagat ttctgatgag gatttagccc ttatccttga tgctgcttgg   120
ttaagcccctt cttctattgg cttagaaggc tggcgctttg tcgttttaga caacaagcct   180
attaaagaag aaatcaagcc ctttgcctgg ggagcccagt atcaactgga aacagctagt   240
cactttattc ttttaatagc cgaaaaacat gcaagatacg atagccctgc tatcaaaaat   300
agccttttac ggcgtggtat caagaaggt gatggtctca acagccgcct aaaactctat   360
gaatctttcc aaaagagga catggatatg gcagataatc ctcgggcact ctttgattgg   420
acagctaaac aaacctatat cgctcttggt aatatgatga tgacagctgc tcttttgggc   480
attgatactt gccctattga aggctttcat tatgataagg tcaatcatat cctagctaag   540
cataatgtga ttgatttaga aaagaaggc attgctagca tgttatccct aggctatcgt   600
ttgcgagatc ccaaacatgc tcaagttcgt aagcctaaag aagaagtgat ttcagtcgtt   660
aaatga                                                              666
```

<210> SEQ ID NO 2
<211> LENGTH: 221
<212> TYPE: PRT
<213> ORGANISM: Streptococcus pyogenes

<400> SEQUENCE: 2

```
Met Asp Gln Thr Ile His His Gln Ile Gln Gln Ala Leu His Phe Arg
1               5                   10                  15

Thr Ala Arg Val Tyr Lys Glu Glu Lys Ile Ser Asp Glu Asp Leu
            20                  25                  30

Ala Leu Ile Leu Asp Ala Ala Trp Leu Ser Pro Ser Ile Gly Leu
        35                  40                  45

Glu Gly Trp Arg Phe Val Val Leu Asp Asn Lys Pro Ile Lys Glu Glu
    50                  55                  60

Ile Lys Pro Phe Ala Trp Gly Ala Gln Tyr Gln Leu Glu Thr Ala Ser
65                  70                  75                  80

His Phe Ile Leu Leu Ile Ala Glu Lys His Ala Arg Tyr Asp Ser Pro
                85                  90                  95

Ala Ile Lys Asn Ser Leu Leu Arg Arg Gly Ile Lys Glu Gly Asp Gly
            100                 105                 110

Leu Asn Ser Arg Leu Lys Leu Tyr Glu Ser Phe Gln Lys Glu Asp Met
        115                 120                 125

Asp Met Ala Asp Asn Pro Arg Ala Leu Phe Asp Trp Thr Ala Lys Gln
    130                 135                 140

Thr Tyr Ile Ala Leu Gly Asn Met Met Thr Ala Ala Leu Leu Gly
145                 150                 155                 160

Ile Asp Thr Cys Pro Ile Glu Gly Phe His Tyr Asp Lys Val Asn His
                165                 170                 175

Ile Leu Ala Lys His Asn Val Ile Asp Leu Glu Lys Glu Gly Ile Ala
            180                 185                 190
```

```
Ser Met Leu Ser Leu Gly Tyr Arg Leu Arg Asp Pro Lys His Ala Gln
        195                 200                 205
Val Arg Lys Pro Lys Glu Glu Val Ile Ser Val Val Lys
    210                 215                 220

<210> SEQ ID NO 3
<211> LENGTH: 1071
<212> TYPE: DNA
<213> ORGANISM: Streptococcus pyogenes

<400> SEQUENCE: 3
atgagacgcg aattattact agaaaaaatt gaaacctaca aggctatcat gccctggtat      60
gttttagatt attaccaatc caaattagct gttccataca gctttaccac cttatatgag     120
tatttaaaag aatacaaacg cttttttgat tggctgatgg atgctgattt aacgcaggcg     180
ccaaagattg ctgatattga cttgagcacg cttgagcacc ttaccaagaa ggatttagag     240
gcctttgtgc tttatttgcg ggaacgacct tctctcaaca cctattccac caaagagggg     300
ctttctcaaa ccactattaa tcggaccttg tctgccttat caagccttta caagtacttg     360
actgaagagg ttgaaaatga ccaaggggag cctatttttt atcggaatgt tatgaaaaaa     420
gtgtcaacaa aaagaaaaa agaaaccctg gcttccagag cggaaaatat taagcagaaa     480
ctgtttttag gtgatgaaac tctagctttc ttggattatg tggataagga atatgagcaa     540
aaattgtcta atcgtgccaa atcttctttc cgtaaaaata aggagaggga tttggctatt     600
attgctctac tacttgcttc tggtgttcgt ttgtctgaag cagtgaatct tgatttaaaa     660
gatgtcaatc taaatatgat gattatcgaa gttattcgca aaggcggaaa acgtgattca     720
gtcaatgtag caggttttgc gaaaggttat ttggagtctt atttagctgt tcgtcagaga     780
cgttacaagg ctgaaaaaca ggatcttgct ttcttttttaa cagaataccg tggcgttcca     840
aatcgaatga tgcttctag tatagaaaag atggttggca agtactctga ggattttaaa     900
attcgtgtga ctcctcacaa attgcgtcat acgctagcga caagactata tgatgctact     960
aaatctcagg tgttagttag tcatcaatta ggccattcct ctactcaagt cacggatctt    1020
tatacccata ttgtcaatga tgagcaaaaa aatgctttag ataacctta a               1071

<210> SEQ ID NO 4
<211> LENGTH: 356
<212> TYPE: PRT
<213> ORGANISM: Streptococcus pyogenes

<400> SEQUENCE: 4

Met Arg Arg Glu Leu Leu Leu Glu Lys Ile Asp Glu Leu Lys Glu Leu
1               5                   10                  15

Met Pro Trp Tyr Val Leu Glu Tyr Tyr Gln Ser Lys Leu Thr Val Pro
            20                  25                  30

Tyr Ser Phe Thr Thr Leu Tyr Glu Tyr Leu Lys Glu Tyr Arg Arg Phe
        35                  40                  45

Phe Glu Trp Leu Ile Asp Ser Gly Val Ser Asn Ala Asn Lys Leu Ala
    50                  55                  60

Asp Ile Pro Leu Glu Thr Leu Glu His Leu Ser Lys Lys Asp Met Glu
65                  70                  75                  80

Ser Phe Ile Leu Tyr Leu Arg Glu Arg Thr Leu Leu Asn Thr Lys Asn
                85                  90                  95

Lys Arg Gln Gly Val Ser Gln Thr Thr Ile Asn Arg Thr Leu Ser Ala
            100                 105                 110
```

```
Leu Ser Ser Leu Tyr Lys Tyr Leu Thr Glu Val Glu Asn Ala Asp
        115                 120                 125
Gly Glu Pro Tyr Phe Tyr Arg Asn Val Met Lys Lys Val Ser Thr Lys
130                 135                 140
Lys Lys Lys Glu Thr Leu Ala Ala Arg Ala Glu Asn Ile Lys Gln Lys
145                 150                 155                 160
Leu Phe Leu Gly Asn Glu Thr Met Glu Phe Leu Glu Tyr Val Asp Cys
                165                 170                 175
Glu Tyr Glu Gln Lys Leu Ser Lys Arg Ala Leu Ser Ser Phe Arg Lys
            180                 185                 190
Asn Lys Glu Arg Asp Leu Ala Ile Ile Ala Leu Leu Leu Ala Ser Gly
        195                 200                 205
Val Arg Leu Ser Glu Ala Val Asn Leu Asp Leu Lys Asp Val Asn Leu
    210                 215                 220
Asn Met Met Ile Ile Glu Val Thr Arg Lys Gly Gly Lys His Asp Ser
225                 230                 235                 240
Val Asn Val Ala Gly Phe Ala Lys Pro Tyr Leu Glu Asn Tyr Ile Thr
                245                 250                 255
Ile Arg Arg Gly Arg Tyr Lys Ala Lys Lys Thr Asp Leu Ala Phe Phe
            260                 265                 270
Leu Ser Glu Tyr Arg Gly Val Pro Asn Arg Met Asp Ala Ser Ser Ile
        275                 280                 285
Glu Lys Met Val Ala Lys Tyr Ser Gln Asp Phe Lys Ile Arg Val Thr
    290                 295                 300
Pro His Lys Leu Arg His Thr Leu Ala Thr Arg Leu Tyr Asp Ala Thr
305                 310                 315                 320
Lys Ser Gln Val Leu Val Ser His Gln Leu Gly His Ala Ser Thr Gln
                325                 330                 335
Val Thr Asp Leu Tyr Thr His Ile Val Asn Asp Glu Gln Lys Asn Ala
            340                 345                 350
Leu Asp Lys Leu
        355

<210> SEQ ID NO 5
<211> LENGTH: 2265
<212> TYPE: DNA
<213> ORGANISM: Streptococcus pyogenes

<400> SEQUENCE: 5
atgacacgct ttacagaata tgttgaaact aaactaggaa atcacttac gcaagccagc      60 aatgaagaga tttatctatc attattaaac tttgtcaaag aagaagctag ccacaaggct     120
aaaaattctg ctaaacgcaa agtttactat atctcagcag agttttttgat tggtaaatta    180 ctatcaaaca acctgattaa cctaggaatt tacaaggaca tcaaagaaga attggcagct    240
gctggcaagt ctatcgcaga agtcgaagat gttgaattag aaccatcact aggtaatggt    300
ggtttaggac gccttgcttc atgttttatt gactctattg catctcttgg gattaatggt    360 gaagggggttg gttttaaacta tcattgtggg ttgtttaagc aagtcttcaa acacaatgag    420
caagaagctg agccaaactt ctggattgaa gatgactcat ggttggttcc aacagacatt    480
tcttacgatg tgcctttttaa gaacttcacc ttgaaatctc gtcttgatcg tattgatgtt    540
ttgggttaca acgcgacac taaaaactac cttaacttgt ttgatatcga gggcgttgat    600
tacgggttaa tcaaagacgg catttctttt gataaaacgc aaattgctaa aaacttgacc    660
```

-continued

```
ttgttcctct acccagacga ttctgacaaa aatggggaat tgctccgtat ttaccaacag      720
tactttatgg tgtcaaatgc agcgcaatta atcattgatg aagctatcga acgtggttca      780
aaccttcatg accttgcaga ctacgcttac gtgcaaatta atgacacgca tccatcaatg      840
gtcatcccag aattaattcg tctcttgact gaaaaacatg gctttgactt tgatgaagcg      900
gtagctgttg tgaaaaatat ggttggttac actaaccaca ctattcttgc agaagccctt      960
gaaaaatggc caactgctta cttaaacgaa gtagtgccac acttggtaac catcattgaa     1020
aaattggatg ctcttgttcg ttcagaagtg tctgatccag ctgttcaaat tattgacgaa     1080
tcaggtcgtg tgcacatggc ccatatggat attcattttg caacaagtgt caatggggta     1140
gcagcactcc acacagaaat cttgaaaaac agcgaattaa aagctttcta tgaccttac      1200
ccagaaaaat tcaacaacaa aaccaacggg attactttcc gtcgttggct agaatttgct     1260
aaccaagact tggctgatta cattaaagaa cttattggcg atgagtactt gactgacgca     1320
acaaaattag aaaaattgat ggcctttgca gatgacaaag ctgttcatgc taaattggct     1380
gaaatcaaat tcaacaacaa attagctctt aaacgttacc ttaaagacaa taaagacatt     1440
gagcttgatg aacattctat tattgatacc caaatcaaac gtttccacga gtacaaacgt     1500
caacagatga atgctctta  cgtgattcac aaatatttgg aaattaaaaa aggcaacctt     1560
ccaaaacgta aaatcactgt tatctttgga ggtaaagcag cgcctgctta cattattgcg     1620
caagacatca ttcacttgat cctttgcttg tctgaattga ttaacaatga ccctgaagta     1680
agcccatacc ttaatgtgca tctagttgaa aattacaacg tgacagtagc agagcacttg     1740
attccagcaa ctgatatttc tgagcaaatt tcactagcat ccaaagaagc ttctggaact     1800
ggtaatatga aattcatgct taacggtgct ttaacacttg gtacaatgga cggtgctaac     1860
gtagaaatcg ctgagcttgc aggcatggag aatatctata cctttggtaa agattctgac     1920
accatcatca acctttatgc gactgcttct tatgtagcaa aagattacta tgataaccac     1980
cctgctatta aagcagcagt gaactttatt atcagtccag aattgctagc atttggcaac     2040
gaagaacgtc ttgatcgtct ttataaagaa ttgatttcaa aagactggtt catgactttg     2100
attgaccttg aagagtacat tgaagtgaaa gaaaaaatgt tagcagacta tgaagaccaa     2160
gatttatgga tgacaaaagt ggtccataac atcgcaaaag ctggattctt ctcatctgac     2220
cgtaccattg agcagtataa cgaagatatt tggcattcac gataa                    2265
```

<210> SEQ ID NO 6
<211> LENGTH: 754
<212> TYPE: PRT
<213> ORGANISM: Streptococcus pyogenes

<400> SEQUENCE: 6

```
Met Thr Arg Phe Thr Glu Tyr Val Glu Thr Lys Leu Gly Lys Ser Leu
1               5                   10                  15
Thr Gln Ala Ser Asn Glu Glu Ile Tyr Leu Ser Leu Leu Asn Phe Val
                20                  25                  30
Lys Glu Glu Ala Ser His Lys Ala Lys Asn Ser Ala Lys Arg Lys Val
            35                  40                  45
Tyr Tyr Ile Ser Ala Glu Phe Leu Ile Gly Lys Leu Leu Ser Asn Asn
        50                  55                  60
Leu Ile Asn Leu Gly Ile Tyr Lys Asp Ile Lys Glu Glu Leu Ala Ala
65                  70                  75                  80
Ala Gly Lys Ser Ile Ala Glu Val Glu Asp Val Glu Leu Glu Pro Ser
                85                  90                  95
```

-continued

Leu Gly Asn Gly Gly Leu Gly Arg Leu Ala Ser Cys Phe Ile Asp Ser
            100                 105                 110

Ile Ala Ser Leu Gly Ile Asn Gly Glu Gly Val Gly Leu Asn Tyr His
        115                 120                 125

Cys Gly Leu Phe Lys Gln Val Phe Lys His Asn Gln Glu Ala Glu
    130                 135                 140

Pro Asn Phe Trp Ile Glu Asp Ser Trp Leu Val Pro Thr Asp Ile
145                 150                 155                 160

Ser Tyr Asp Val Pro Phe Lys Asn Phe Thr Leu Lys Ser Arg Leu Asp
                165                 170                 175

Arg Ile Asp Val Leu Gly Tyr Lys Arg Asp Thr Lys Asn Tyr Leu Asn
            180                 185                 190

Leu Phe Asp Ile Glu Gly Val Asp Tyr Gly Leu Ile Lys Asp Gly Ile
        195                 200                 205

Ser Phe Asp Lys Thr Gln Ile Ala Lys Asn Leu Thr Leu Phe Leu Tyr
    210                 215                 220

Pro Asp Asp Ser Asp Lys Asn Gly Glu Leu Leu Arg Ile Tyr Gln Gln
225                 230                 235                 240

Tyr Phe Met Val Ser Asn Ala Ala Gln Leu Ile Ile Asp Glu Ala Ile
                245                 250                 255

Glu Arg Gly Ser Asn Leu His Asp Leu Ala Asp Tyr Ala Tyr Val Gln
            260                 265                 270

Ile Asn Asp Thr His Pro Ser Met Val Ile Pro Glu Leu Ile Arg Leu
        275                 280                 285

Leu Thr Glu Lys His Gly Phe Asp Phe Asp Glu Ala Val Ala Val Val
    290                 295                 300

Lys Asn Met Val Gly Tyr Thr Asn His Thr Ile Leu Ala Glu Ala Leu
305                 310                 315                 320

Glu Lys Trp Pro Thr Ala Tyr Leu Asn Glu Val Val Pro His Leu Val
                325                 330                 335

Thr Ile Ile Glu Lys Leu Asp Ala Leu Val Arg Ser Glu Val Ser Asp
            340                 345                 350

Pro Ala Val Gln Ile Ile Asp Glu Ser Gly Arg Val His Met Ala His
        355                 360                 365

Met Asp Ile His Phe Ala Thr Ser Val Asn Gly Val Ala Ala Leu His
    370                 375                 380

Thr Glu Ile Leu Lys Asn Ser Glu Leu Lys Ala Phe Tyr Asp Leu Tyr
385                 390                 395                 400

Pro Glu Lys Phe Asn Asn Lys Thr Asn Gly Ile Thr Phe Arg Arg Trp
                405                 410                 415

Leu Glu Phe Ala Asn Gln Asp Leu Ala Asp Tyr Ile Lys Glu Leu Ile
            420                 425                 430

Gly Asp Glu Tyr Leu Thr Asp Ala Thr Lys Leu Glu Lys Leu Met Ala
        435                 440                 445

Phe Ala Asp Asp Lys Ala Val His Ala Lys Leu Ala Glu Ile Lys Phe
    450                 455                 460

Asn Asn Lys Leu Ala Leu Lys Arg Tyr Leu Lys Asp Asn Lys Asp Ile
465                 470                 475                 480

Glu Leu Asp Glu His Ser Ile Ile Asp Thr Gln Ile Lys Arg Phe His
                485                 490                 495

Glu Tyr Lys Arg Gln Gln Met Asn Ala Leu Tyr Val Ile His Lys Tyr
            500                 505                 510

```
Leu Glu Ile Lys Lys Gly Asn Leu Pro Lys Arg Lys Ile Thr Val Ile
            515                 520                 525
Phe Gly Gly Lys Ala Ala Pro Ala Tyr Ile Ile Ala Gln Asp Ile Ile
        530                 535                 540
His Leu Ile Leu Cys Leu Ser Glu Leu Ile Asn Asn Asp Pro Glu Val
545                 550                 555                 560
Ser Pro Tyr Leu Asn Val His Leu Val Glu Asn Tyr Asn Val Thr Val
                565                 570                 575
Ala Glu His Leu Ile Pro Ala Thr Asp Ile Ser Glu Gln Ile Ser Leu
            580                 585                 590
Ala Ser Lys Glu Ala Ser Gly Thr Gly Asn Met Lys Phe Met Leu Asn
        595                 600                 605
Gly Ala Leu Thr Leu Gly Thr Met Asp Gly Ala Asn Val Glu Ile Ala
    610                 615                 620
Glu Leu Ala Gly Met Glu Asn Ile Tyr Thr Phe Gly Lys Asp Ser Asp
625                 630                 635                 640
Thr Ile Ile Asn Leu Tyr Ala Thr Ala Ser Tyr Val Ala Lys Asp Tyr
                645                 650                 655
Tyr Asp Asn His Pro Ala Ile Lys Ala Ala Val Asn Phe Ile Ile Ser
            660                 665                 670
Pro Glu Leu Leu Ala Phe Gly Asn Glu Glu Arg Leu Asp Arg Leu Tyr
        675                 680                 685
Lys Glu Leu Ile Ser Lys Asp Trp Phe Met Thr Leu Ile Asp Leu Glu
    690                 695                 700
Glu Tyr Ile Glu Val Lys Glu Lys Met Leu Ala Asp Tyr Glu Asp Gln
705                 710                 715                 720
Asp Leu Trp Met Thr Lys Val Val His Asn Ile Ala Lys Ala Gly Phe
                725                 730                 735
Phe Ser Ser Asp Arg Thr Ile Glu Gln Tyr Asn Glu Asp Ile Trp His
            740                 745                 750
Ser Arg

<210> SEQ ID NO 7
<211> LENGTH: 1371
<212> TYPE: DNA
<213> ORGANISM: Streptococcus pyogenes

<400> SEQUENCE: 7
atgaaacaaa aaatgtata tatcgtcatt ggattcatgc tatttgcgct atttttgga      60
gcagcaaacc tcatttaccc agctttttta ggcatctact caggtcatca gattctatgg     120
tctatcattg ttttgtttt aactggtgtc tccttgcctt tactcggtgt cattgctgtt     180
gctaaatctg gatcaggcga tgttgaaagt ttggcacgcc ccatctctaa atggtatgca     240
atcttctatt cttccatttt gtatttatct attggcccat tttttgctat tccaagaaca     300
ggagccactt cttttttcagt cggtatcgct cctatcttag gagataatac aaccaataaa     360
gctatttatg ctatactatt ttttggtctg tcctacttcc ttgctatcaa acctagtaaa     420
ctagctgaaa atatcggaaa attttttaacg ccaacgttgt tagttgttat ttctattttg     480
gttatcgcgt cctttgtcca tcctgctgga aattacggtg atgcttttaa cgctggggtc     540
ggtgttaata atgcctttaa agattttcct tttatagcag gattaattca aggttatggc     600
actatggatg cactagcttc tcttgttttt gctatttag tcattgaggc taccaaacaa     660
tttggcgcta agacggacaa agaaatgacc aaaataacac ttatttctgg ggctattgcc     720
```

-continued

```
attttgctat tagcacttgt ctatatcttt gtcggtcgta ttggagcaac atcacaatca    780
ttatttcctt ttattgatgg cagctttacc cttcatggta atccagttaa tggcggtcaa    840
atcttaagtc atgcttctcg tttttaccta ggtggcatcg acaagcatt tctagctgtt     900 gtgattttcc tggcctgtct aaccacttca acaggcttaa tcacgtcaag tgctgaatac    960
ttccataaat tagtgcctgc tttatctcat attgctgggg caactatctt tactttacta   1020
tcagctttct tttattttgg tggcttatca gtcattatca actggtcagc tcctgtttta   1080
ttccttttat acccattaac agtcgattta attttccttg ttttggcaca aaaatgcttc   1140
aataatgatc ctattgtcta tcgaactaca attggtctaa cctttattcc tgccatattt   1200
gatgcactcc taacactatc acaaatgact ggattatttc atttaccaga agccgttgta   1260
acttttttcc aaaaaactgt tccactaggg caattctcaa tgggatggat tatctttgct   1320
gctattggtt ttttaatagg gcttatacta agtaaaacga agaaaagcta a            1371
```

<210> SEQ ID NO 8
<211> LENGTH: 456
<212> TYPE: PRT
<213> ORGANISM: Streptococcus pyogenes

<400> SEQUENCE: 8

```
Met Lys Gln Lys Asn Val Tyr Ile Val Ile Gly Phe Met Leu Phe Ala
1               5                   10                  15

Leu Phe Phe Gly Ala Ala Asn Leu Ile Tyr Pro Ala Phe Leu Gly Ile
                20                  25                  30

Tyr Ser Gly His Gln Ile Leu Trp Ser Ile Ile Gly Phe Cys Leu Thr
            35                  40                  45

Gly Val Ser Leu Pro Leu Leu Gly Val Ile Ala Val Ala Lys Ser Gly
        50                  55                  60

Ser Gly Asp Val Glu Ser Leu Ala Arg Pro Ile Ser Lys Trp Tyr Ala
65                  70                  75                  80

Ile Phe Tyr Ser Ser Ile Leu Tyr Leu Ser Ile Gly Pro Phe Phe Ala
                85                  90                  95

Ile Pro Arg Thr Gly Ala Thr Ser Phe Ser Val Gly Ile Ala Pro Ile
                100                 105                 110

Leu Gly Asp Asn Thr Thr Asn Lys Ala Ile Tyr Ala Ile Leu Phe Phe
            115                 120                 125

Gly Leu Ser Tyr Phe Leu Ala Ile Lys Pro Ser Lys Leu Ala Glu Asn
        130                 135                 140

Ile Gly Lys Phe Leu Thr Pro Thr Leu Leu Val Val Ile Ser Ile Leu
145                 150                 155                 160

Val Ile Ala Ser Phe Val His Pro Ala Gly Asn Tyr Gly Asp Ala Phe
                165                 170                 175

Asn Ala Gly Val Gly Val Asn Asn Ala Phe Lys Asp Phe Pro Phe Ile
            180                 185                 190

Ala Gly Leu Ile Gln Gly Tyr Gly Thr Met Asp Ala Leu Ala Ser Leu
        195                 200                 205

Val Phe Ala Ile Leu Val Ile Glu Ala Thr Lys Gln Phe Gly Ala Lys
    210                 215                 220

Thr Asp Lys Glu Met Thr Lys Ile Thr Leu Ile Ser Gly Ala Ile Ala
225                 230                 235                 240

Ile Leu Leu Leu Ala Leu Val Tyr Ile Phe Val Gly Arg Ile Gly Ala
                245                 250                 255

Thr Ser Gln Ser Leu Phe Pro Phe Ile Asp Gly Ser Phe Thr Leu His
```

-continued

```
                260                 265                 270
Gly Asn Pro Val Asn Gly Gln Ile Leu Ser His Ala Ser Arg Phe
            275                 280                 285
Tyr Leu Gly Gly Ile Gly Gln Ala Phe Leu Ala Val Ile Phe Leu
            290                 295                 300
Ala Cys Leu Thr Thr Ser Thr Gly Leu Ile Thr Ser Ala Glu Tyr
305                 310                 315                 320
Phe His Lys Leu Val Pro Ala Leu Ser His Ile Ala Trp Ala Thr Ile
                325                 330                 335
Phe Thr Leu Leu Ser Ala Phe Tyr Phe Gly Gly Leu Ser Val Ile
            340                 345                 350
Ile Asn Trp Ser Ala Pro Val Leu Phe Leu Leu Tyr Pro Leu Thr Val
                355                 360                 365
Asp Leu Ile Phe Leu Val Leu Ala Gln Lys Cys Phe Asn Asn Asp Pro
            370                 375                 380
Ile Val Tyr Arg Thr Thr Ile Gly Leu Thr Phe Ile Pro Ala Ile Phe
385                 390                 395                 400
Asp Ala Leu Leu Thr Leu Ser Gln Met Thr Gly Leu Phe His Leu Pro
                405                 410                 415
Glu Ala Val Val Thr Phe Phe Gln Lys Thr Val Pro Leu Gly Gln Phe
            420                 425                 430
Ser Met Gly Trp Ile Ile Phe Ala Ala Ile Gly Phe Leu Ile Gly Leu
            435                 440                 445
Ile Leu Ser Lys Thr Lys Lys Ser
    450                 455

<210> SEQ ID NO 9
<211> LENGTH: 441
<212> TYPE: DNA
<213> ORGANISM: Streptococcus pyogenes

<400> SEQUENCE: 9
atggggattt tagaaaaaaa acttgataac ttagtaaata ctattttatt aaaagcagaa      60
aatcagcatg agttattatt tggagcttgt caaagtgacg ttaagcttac taatacgcaa     120
gaacatattt taatgttact atctcagcaa cgtctcacta atacagattt ggctaaggca     180
ttaaatatta gtcaggcggc agtaactaag gctatcaaga gtttggtcaa acaagacatg     240
ttagcaggaa ctaaggatac ggttgatgct agggtgactt attttgaatt aaccgagtta     300
gctaagccta ttgcgtcaga acatacccat catcatgatg aaaccttaaa tgtttacaac     360
cgtttattac aaaaattctc cgcgaaagaa ttagagattg tagataagtt tgtaacagtt     420
tttgctgagg aattagaagg g                                              441

<210> SEQ ID NO 10
<211> LENGTH: 147
<212> TYPE: PRT
<213> ORGANISM: Streptococcus pyogenes

<400> SEQUENCE: 10

Met Gly Ile Leu Glu Lys Lys Leu Asp Asn Leu Val Asn Thr Ile Leu
1               5                   10                  15
Leu Lys Ala Glu Asn Gln His Glu Leu Leu Phe Gly Ala Cys Gln Ser
            20                  25                  30
Asp Val Lys Leu Thr Asn Thr Gln Glu His Ile Leu Met Leu Leu Ser
        35                  40                  45
```

```
Gln Gln Arg Leu Thr Asn Thr Asp Leu Ala Lys Ala Leu Asn Ile Ser
        50                  55                  60

Gln Ala Ala Val Thr Lys Ala Ile Lys Ser Leu Val Lys Gln Asp Met
65                  70                  75                  80

Leu Ala Gly Thr Lys Asp Thr Val Asp Ala Arg Val Thr Tyr Phe Glu
                85                  90                  95

Leu Thr Glu Leu Ala Lys Pro Ile Ala Ser Glu His Thr His His His
            100                 105                 110

Asp Glu Thr Leu Asn Val Tyr Asn Arg Leu Leu Gln Lys Phe Ser Ala
            115                 120                 125

Lys Glu Leu Glu Ile Val Asp Lys Phe Val Thr Val Phe Ala Glu Glu
        130                 135                 140

Leu Glu Gly
145

<210> SEQ ID NO 11
<211> LENGTH: 815
<212> TYPE: DNA
<213> ORGANISM: Streptococcus pyogenes

<400> SEQUENCE: 11
atgcttgata tttttattcta tgatttcatg caacgggcgg taatggcggt agttgccatt     60 agtattttg ctccgatttt aggtatttte cttattttac gtcgtcaaag tttgatgagc     120 gatacccta gtcatgtttc tttggctggg gtagcgcttg gggtagtcct tggtatttca     180
ccaaccatca ctactattat tgttgtggtt ttagctgcta ttttgttaga ataccctgcgt    240 gtagtttaca acactacat ggagatttca acggcgattt tgatgtcact tggcttggcc     300
ctatctctga ttattatgag taagtcgcat agttcatcaa gcatgagttt agaacaatac     360 cttttttggat cgatcatcac gattagtatg aacaagttg tcgccttgtt tgctattgct     420
gcgattattt taatcttgac cgttctcttc attagaccga tgtacattct gacctttgat     480
gaagatactg cttttgtaga tggtttgccc gttcgcttga tgtctgttct attcaatatc     540
gtcactgggg ttgctattgc tttgaccatt ccagcagcag gagcactttt ggtttctacc     600
attatggtct tgccagcaag tatcgcaatg agattgggta aaaactttaa aacagttatc     660
ttactgggaa ttgtcatcgg ttttagcggt atgttatctg gtattttctt atcttatttc     720
tttgaaacgc cagctagtgc cactattacc atgattttca ttagtatttt cctcttagtt     780
agtctaggtg gaatgcttaa aaaacggtta tttaa                                 815

<210> SEQ ID NO 12
<211> LENGTH: 239
<212> TYPE: PRT
<213> ORGANISM: Streptococcus pyogenes

<400> SEQUENCE: 12

Met Arg Tyr Ile Ser Val Lys Asn Leu Ser Phe Gln Tyr Glu Ser Glu
1               5                   10                  15

Pro Val Leu Glu Gly Ile Thr Tyr His Leu Asp Ser Gly Glu Phe Val
                20                  25                  30

Thr Met Thr Gly Glu Asn Gly Ala Ala Lys Ser Thr Leu Ile Lys Ala
            35                  40                  45

Thr Leu Gly Ile Leu Gln Pro Lys Ala Gly Arg Val Thr Ile Ala Lys
        50                  55                  60

Lys Asn Lys Asp Gly Lys Gln Leu Arg Ile Ala Tyr Leu Pro Gln Gln
65                  70                  75                  80
```

```
Val Ala Ser Phe Asn Ala Gly Phe Pro Ser Thr Val Tyr Glu Phe Val
                85                  90                  95

Lys Ser Gly Arg Tyr Pro Arg Ser Gly Trp Phe Arg His Leu Asn Lys
            100                 105                 110

His Asp Glu Glu His Val Gln Ala Ser Leu Glu Ala Val Gly Met Trp
        115                 120                 125

Glu Asn Arg His Lys Arg Ile Gly Ser Leu Ser Gly Gly Gln Lys Gln
    130                 135                 140

Arg Val Val Ile Ala Arg Met Phe Ala Ser Asp Pro Asp Ile Phe Val
145                 150                 155                 160

Leu Asp Glu Pro Thr Thr Gly Met Asp Ser Gly Thr Thr Asp Thr Phe
                165                 170                 175

Tyr Glu Leu Met His His Ser Ala His Gln His Gly Lys Ser Val Leu
            180                 185                 190

Met Ile Thr His Asp Pro Glu Glu Val Lys Ala Tyr Ala Asp Arg Asn
        195                 200                 205

Ile His Leu Val Arg Asn Gln Lys Leu Pro Trp Arg Cys Phe Asn Ile
    210                 215                 220

His Glu Ala Glu Thr Asp Asp Glu Lys Gly Gly His Gly His Ala
225                 230                 235

<210> SEQ ID NO 13
<211> LENGTH: 681
<212> TYPE: DNA
<213> ORGANISM: Streptococcus pyogenes

<400> SEQUENCE: 13
atgtattcta taaaatgtga tgataataaa gccatgccaa gagaacgttt gatgcgacta      60
ggagcagagt ctctaagtaa tcaagaatta ttagcaattt tattacgaac aggtaataaa     120
gaaaagcatg tcttagagct gtcatcctat cttttatcgc atttagacag tctggcagat     180
tttaaaaaga tgtctttgca agaattacaa catttggcag gtataggaaa agttaaagcg     240
attgaaatta aagctatgat tgagttggtt tcccgaattt tagcgacaga taagacatta     300
actgatagcg tattaaccag tgttcaggtc gctgaaaaaa tgatggcagc tttaggagat     360
aaaaaacaag agcatttagt cgtattgtat ttagataatc aaaatcgtat tattgaagaa     420
aaaactattt ttattgggac tgtccgacgt tcacttgcag aaccaagaga aattttatac     480
tatgcctgta aaaatatggc gactagtctc attgttattc ataatcatcc ttcaggaaat     540
attgaaccta gttctaacga ttattgcttt actgaaaaaa taaaacgatc atgtgaagat     600
ttaggcatta tctgtctaga tcacattatc gttagctata agattattta gttttcga      660 gaaaaatcaa cccttttta a                                                681

<210> SEQ ID NO 14
<211> LENGTH: 226
<212> TYPE: PRT
<213> ORGANISM: Streptococcus pyogenes

<400> SEQUENCE: 14

Met Tyr Ser Ile Lys Cys Asp Asp Asn Lys Ala Met Pro Arg Glu Arg
1               5                   10                  15

Leu Met Arg Leu Gly Ala Glu Ser Leu Ser Asn Gln Glu Leu Leu Ala
            20                  25                  30

Ile Leu Leu Arg Thr Gly Asn Lys Glu Lys His Val Leu Glu Leu Ser
        35                  40                  45
```

Ser Tyr Leu Leu Ser His Leu Asp Ser Leu Ala Asp Phe Lys Lys Met
    50                  55                  60

Ser Leu Gln Glu Leu Gln His Leu Ala Gly Ile Gly Lys Val Lys Ala
65                  70                  75                  80

Ile Glu Ile Lys Ala Met Ile Glu Leu Val Ser Arg Ile Leu Ala Thr
                85                  90                  95

Asp Lys Thr Leu Thr Asp Ser Val Leu Thr Ser Val Gln Val Ala Glu
            100                 105                 110

Lys Met Met Ala Ala Leu Gly Asp Lys Lys Gln Glu His Leu Val Val
            115                 120                 125

Leu Tyr Leu Asp Asn Gln Asn Arg Ile Ile Glu Glu Lys Thr Ile Phe
    130                 135                 140

Ile Gly Thr Val Arg Arg Ser Leu Ala Glu Pro Arg Glu Ile Leu Tyr
145                 150                 155                 160

Tyr Ala Cys Lys Asn Met Ala Thr Ser Leu Ile Val Ile His Asn His
                165                 170                 175

Pro Ser Gly Asn Ile Glu Pro Ser Ser Asn Asp Tyr Cys Phe Thr Glu
            180                 185                 190

Lys Ile Lys Arg Ser Cys Glu Asp Leu Gly Ile Ile Cys Leu Asp His
        195                 200                 205

Ile Ile Val Ser Tyr Lys Asp Tyr Tyr Ser Phe Arg Glu Lys Ser Thr
    210                 215                 220

Leu Phe
225

<210> SEQ ID NO 15
<211> LENGTH: 410
<212> TYPE: DNA
<213> ORGANISM: Streptococcus pyogenes

<400> SEQUENCE: 15
atgatgttac gaaaatttaa aattaccatt gacggtaaag agtatcttgt agaaatggaa      60
gaaatcggtg ctcctgccca agcagctgcc cccgctcaac caatatccac tccagtacct     120
gtccctactg aagcaagccc acaagtggag gaagcgcaag caccacagcc agtagctgca     180
gcgggagcgg atgccattcc atcaccaatg cctggaacca tcttaaaagt cttagtagca     240
gtgggagacc aagtaactga aaatcagcca ctattgattt tagaagccat gagatggaa      300 aatgagattg tggcctcatc agcaggaacc attacagcta tccacgtcgg tccaggtcaa     360
gtggtcaatc ctggtgatgg tctcattaca attggttaat agtactataa                410

<210> SEQ ID NO 16
<211> LENGTH: 134
<212> TYPE: PRT
<213> ORGANISM: Streptococcus pyogenes

<400> SEQUENCE: 16

Met Met Leu Arg Lys Phe Lys Ile Thr Ile Asp Gly Lys Glu Tyr Leu
1               5                   10                  15

Val Glu Met Glu Glu Ile Gly Ala Pro Ala Gln Ala Ala Pro Ala
            20                  25                  30

Gln Pro Ile Ser Thr Pro Val Pro Val Pro Thr Glu Ala Ser Pro Gln
        35                  40                  45

Val Glu Glu Ala Gln Ala Pro Gln Pro Val Ala Ala Ala Gly Ala Asp
    50                  55                  60

```
Ala Ile Pro Ser Pro Met Pro Gly Thr Ile Leu Lys Val Leu Val Ala
 65                  70                  75                  80

Val Gly Asp Gln Val Thr Glu Asn Gln Pro Leu Leu Ile Leu Glu Ala
                 85                  90                  95

Met Lys Met Glu Asn Glu Ile Val Ala Ser Ser Ala Gly Thr Ile Thr
            100                 105                 110

Ala Ile His Val Gly Pro Gly Gln Val Val Asn Pro Gly Asp Gly Leu
        115                 120                 125

Ile Thr Ile Gly Tyr Tyr
        130

<210> SEQ ID NO 17
<211> LENGTH: 1533
<212> TYPE: DNA
<213> ORGANISM: Streptococcus pyogenes

<400> SEQUENCE: 17
atggtaacaa ataaactcgg tagagatatt cctcaaccat acgccgacca atacggtgtc      60
tttgaaggag aactcgcaaa tatcaaacag tatgacgaat caagtcgccg tattaaacca     120
gttaagcctg gagattctaa attactagga tctgttcgtg aagcgattga aaaaacaggt     180
ttaacagatg gcatgaccat ttcttttcca caccatttcc gtgaagggga tttcattatg     240
aatatggtct tggaggaaat tgccaaaatg ggcattaaaa acctgtctat tgccccaagt     300
tccatcgcta atgtacatga gcctttgatt gatcacatca aaaatggtgt ggtcactaac     360
atcacttcat ctggtcttcg tgacaaagta ggggcagcca tctcagaagg actaatggaa     420
aatcctgtgg ttattcgctc ccatggtggt cgcgctcgtg ccattgctag tggggatatc     480
catattgatg ttgcctttct gggcgcccca agttcagatg cttacggaaa tgttaatggg     540
acaaaaggga agcaacctg tggttctttg gctatgcca tgattgatgc aaatatgcg     600 gatcaggtgg ttatcttgac agataatttg gttccttatc ctaatacccc aatcagcatt     660
cctcaaacag atgttgacta tgtggtaaca gtggatgcta tcggagatcc tcaaggaatc     720
gccaaagggg caactcgttt tacgaaaaat cctaagaaac tcttaattgc agaatacgcc     780
gctaaagtaa tcaccaactc tccttatttt aaagaaggat tctcttttcca aactggaaca     840 ggtggcgctt ctttggcagt aacccgtttc atgcgtgaag ctatgattaa agaaaatatc     900
aaagctagct ttgctcttgg tggtattacc aatgctatgg tggagttgct cgaagaagaa     960
ctggttgaaa aaattcttga tgtccaagac tttgatcacc catcagctgt ttctcttggt    1020
aagcatgctg aacattatga aattgatgcc aacatgtatg cctcaccttt gagcaagggt    1080
gctgttatca atcaattaga cacttgtatt ttatcagccc ttgaagttga tactaacttc    1140
aatgttaatg tgatgacagg atctgacggc gtgattcgtg gcgcttctgg aggacactgc    1200
gacactgcct ttgcggctaa gatgagtttg gttatttcac cacttatccg cggacgcatc    1260
ccaacttttg tagatgaggt taatacggtc attacaccag gaacaagtgt cgatgtgatc    1320
gtcacagaag tgggaattgc cattaaccca atcgtcaag acttagtaga ccatttcaaa    1380
tccctcaatg tgccacaatt tagtattgag gagctaaaag agaaggctta cgccatcgtt    1440
ggcacacctg agcgtattca atatggtgat aaggttgttg ctcttattga ataccgtgac    1500
ggtagcctca tggatgtggt ttacaatgtg taa                                 1533

<210> SEQ ID NO 18
<211> LENGTH: 510
<212> TYPE: PRT
```

-continued

<213> ORGANISM: Streptococcus pyogenes

<400> SEQUENCE: 18

```
Met Val Thr Asn Lys Leu Gly Arg Asp Ile Pro Gln Pro Tyr Ala Asp
1               5                   10                  15

Gln Tyr Gly Val Phe Glu Gly Leu Ala Asn Ile Lys Gln Tyr Asp
            20                  25                  30

Glu Ser Ser Arg Arg Ile Lys Pro Val Lys Pro Gly Asp Ser Lys Leu
        35                  40                  45

Leu Gly Ser Val Arg Glu Ala Ile Glu Lys Thr Gly Leu Thr Asp Gly
    50                  55                  60

Met Thr Ile Ser Phe His His His Phe Arg Glu Gly Asp Phe Ile Met
65                  70                  75                  80

Asn Met Val Leu Glu Glu Ile Ala Lys Met Gly Ile Lys Asn Leu Ser
                85                  90                  95

Ile Ala Pro Ser Ser Ile Ala Asn Val His Glu Pro Leu Ile Asp His
            100                 105                 110

Ile Lys Asn Gly Val Val Thr Asn Ile Thr Ser Ser Gly Leu Arg Asp
        115                 120                 125

Lys Val Gly Ala Ala Ile Ser Glu Gly Leu Met Glu Asn Pro Val Val
    130                 135                 140

Ile Arg Ser His Gly Gly Arg Ala Arg Ala Ile Ala Ser Gly Asp Ile
145                 150                 155                 160

His Ile Asp Val Ala Phe Leu Gly Ala Pro Ser Ser Asp Ala Tyr Gly
                165                 170                 175

Asn Val Asn Gly Thr Lys Gly Lys Ala Thr Cys Gly Ser Leu Gly Tyr
            180                 185                 190

Ala Met Ile Asp Ala Lys Tyr Ala Asp Gln Val Val Ile Leu Thr Asp
        195                 200                 205

Asn Leu Val Pro Tyr Pro Asn Thr Pro Ile Ser Ile Pro Gln Thr Asp
    210                 215                 220

Val Asp Tyr Val Val Thr Val Asp Ala Ile Gly Asp Pro Gln Gly Ile
225                 230                 235                 240

Ala Lys Gly Ala Thr Arg Phe Thr Lys Asn Pro Lys Glu Leu Leu Ile
                245                 250                 255

Ala Glu Tyr Ala Ala Lys Val Ile Thr Asn Ser Pro Tyr Phe Lys Glu
            260                 265                 270

Gly Phe Ser Phe Gln Thr Gly Thr Gly Gly Ala Ser Leu Ala Val Thr
        275                 280                 285

Arg Phe Met Arg Glu Ala Met Ile Lys Glu Asn Ile Lys Ala Ser Phe
    290                 295                 300

Ala Leu Gly Gly Ile Thr Asn Ala Met Val Glu Leu Leu Glu Glu Glu
305                 310                 315                 320

Leu Val Glu Lys Ile Leu Asp Val Gln Asp Phe Asp His Pro Ser Ala
                325                 330                 335

Val Ser Leu Gly Lys His Ala Glu His Tyr Glu Ile Asp Ala Asn Met
            340                 345                 350

Tyr Ala Ser Pro Leu Ser Lys Gly Ala Val Ile Asn Gln Leu Asp Thr
        355                 360                 365

Cys Ile Leu Ser Ala Leu Glu Val Asp Thr Asn Phe Asn Val Asn Val
    370                 375                 380

Met Thr Gly Ser Asp Gly Val Ile Arg Gly Ala Ser Gly Gly His Cys
385                 390                 395                 400
```

Asp Thr Ala Phe Ala Ala Lys Met Ser Leu Val Ile Ser Pro Leu Ile
            405                 410                 415

Arg Gly Arg Ile Pro Thr Phe Val Asp Glu Val Asn Thr Val Ile Thr
            420                 425                 430

Pro Gly Thr Ser Val Asp Val Ile Val Thr Glu Val Gly Ile Ala Ile
            435                 440                 445

Asn Pro Asn Arg Gln Asp Leu Val Asp His Phe Lys Ser Leu Asn Val
450                 455                 460

Pro Gln Phe Ser Ile Glu Glu Leu Lys Glu Lys Ala Tyr Ala Ile Val
465                 470                 475                 480

Gly Thr Pro Glu Arg Ile Gln Tyr Gly Asp Lys Val Val Ala Leu Ile
                485                 490                 495

Glu Tyr Arg Asp Gly Ser Leu Met Asp Val Val Tyr Asn Val
            500                 505                 510

<210> SEQ ID NO 19
<211> LENGTH: 888
<212> TYPE: DNA
<213> ORGANISM: Streptococcus pyogenes

<400> SEQUENCE: 19
atggaacgtt taagaagaac aatgatgttt gtgcctggtg ccaatgcagc catgcttcga      60
gatgctcctt tatttggcgc tgattcaatc atgtttgact ggaagattc tgtttcactc     120
aaagaaaaag acacctctag agctctcgtt cattttgcgc ttaaaacttt tgattattca     180
agcgttgaaa cggttgttcg tgtgaatggt cttgattctt gtgggctttt agacatcgaa     240
gctgttgttt ggcaggtgt caacgtgatt cgtcttccaa aaacagagac tgctcaagat     300
attattgatg tggaggctgt tattgaacgt gtcgaacgcg agaacagcat tgaagttggt     360
cgcacacgta tgatggcagc cattgaatca gccgaaggtg tcctaaatgc tcgtgagatt     420
gccaaagctt ctaagcgctt gattggtatt gctcttggag cagaagacta tgtcacgaat     480
atgaaaacgc gtcgttaccc agatggtcaa gaattattct ttgctcgtag catgattta     540
cacgctgctc gtgctgctgg aattgctgcc attgatactg tttattctga tgtcaataat     600
accgaagggt tccaaaacga gttcgcatg atcaaacagt taggatttga tggtaaatcg     660
gtcatcaacc ctcgccaaat tcctctggtc aatgagattt ataccccaac aaaaaaagaa     720
attgaccatg ccaaacaagt catctgggca attcgtgaag ctgaaagcaa aggctctggc     780
gttatttcct aaatggaaaa atgggttgat aaaccaatcg ttgaacgtgc agaacgtgtg     840
attgccctag caacagcagc aggtgtttta tctgaggagg atatttaa                 888

<210> SEQ ID NO 20
<211> LENGTH: 295
<212> TYPE: PRT
<213> ORGANISM: Streptococcus pyogenes

<400> SEQUENCE: 20

Met Glu Arg Leu Arg Arg Thr Met Met Phe Val Pro Gly Ala Asn Ala
1                   5                   10                  15

Ala Met Leu Arg Asp Ala Pro Leu Phe Gly Ala Asp Ser Ile Met Phe
            20                  25                  30

Asp Leu Glu Asp Ser Val Ser Leu Lys Glu Lys Asp Thr Ser Arg Ala
        35                  40                  45

Leu Val His Phe Ala Leu Lys Thr Phe Asp Tyr Ser Ser Val Glu Thr
    50                  55                  60

```
Val Val Arg Val Asn Gly Leu Asp Ser Cys Gly Ala Leu Asp Ile Glu
 65                  70                  75                  80

Ala Val Val Leu Ala Gly Val Asn Val Ile Arg Leu Pro Lys Thr Glu
                 85                  90                  95

Thr Ala Gln Asp Ile Ile Asp Val Glu Ala Val Ile Glu Arg Val Glu
            100                 105                 110

Arg Glu Asn Ser Ile Glu Val Gly Arg Thr Arg Met Met Ala Ala Ile
        115                 120                 125

Glu Ser Ala Glu Gly Val Leu Asn Ala Arg Glu Ile Ala Lys Ala Ser
    130                 135                 140

Lys Arg Leu Ile Gly Ile Ala Leu Gly Ala Glu Asp Tyr Val Thr Asn
145                 150                 155                 160

Met Lys Thr Arg Arg Tyr Pro Asp Gly Gln Glu Leu Phe Phe Ala Arg
                165                 170                 175

Ser Met Ile Leu His Ala Ala Arg Ala Ala Gly Ile Ala Ala Ile Asp
            180                 185                 190

Thr Val Tyr Ser Asp Val Asn Asn Thr Glu Gly Phe Gln Asn Glu Val
        195                 200                 205

Arg Met Ile Lys Gln Leu Gly Phe Asp Gly Lys Ser Val Ile Asn Pro
    210                 215                 220

Arg Gln Ile Pro Leu Val Asn Glu Ile Tyr Thr Pro Thr Lys Lys Glu
225                 230                 235                 240

Ile Asp His Ala Lys Gln Val Ile Trp Ala Ile Arg Glu Ala Glu Ser
                245                 250                 255

Lys Gly Ser Gly Val Ile Ser Leu Asn Gly Lys Met Val Asp Lys Pro
            260                 265                 270

Ile Val Glu Arg Ala Glu Arg Val Ile Ala Leu Ala Thr Ala Ala Gly
        275                 280                 285

Val Leu Ser Glu Glu Asp Ile
    290                 295

<210> SEQ ID NO 21
<211> LENGTH: 309
<212> TYPE: DNA
<213> ORGANISM: Streptococcus pyogenes

<400> SEQUENCE: 21
atggatatta aacaaactgc cgttgctggt tcacttgaat caagtgacct aatgattaca        60 gtatcccta  atgacgagca aaccattaca ataaccctag acagtagtgt tgaaaaacaa       120
tttggcaatc acattcgtca actcattcat caaaccctag tgaatttgaa ggtgacggct       180
gctaaagtag aggctgttga taaaggtgca ttagattgca ccattcaagc gagaaccatc       240
gcagctgttc atcgcgctgc tggtattgac caatacgatt ggaaggagat tgactcatgg       300
aacgtttaa                                                              309

<210> SEQ ID NO 22
<211> LENGTH: 102
<212> TYPE: PRT
<213> ORGANISM: Streptococcus pyogenes

<400> SEQUENCE: 22

Met Asp Ile Lys Gln Thr Ala Val Ala Gly Ser Leu Glu Ser Ser Asp
  1               5                  10                  15

Leu Met Ile Thr Val Ser Pro Asn Asp Glu Gln Thr Ile Thr Ile Thr
             20                  25                  30
```

Leu Asp Ser Val Glu Lys Gln Phe Gly Asn His Ile Arg Gln Leu
        35                  40                  45

Ile His Gln Thr Leu Val Asn Leu Lys Val Thr Ala Ala Lys Val Glu
50                  55                  60

Ala Val Asp Lys Gly Ala Leu Asp Cys Thr Ile Gln Ala Arg Thr Ile
65                  70                  75                  80

Ala Ala Val His Arg Ala Ala Gly Ile Asp Gln Tyr Asp Trp Lys Glu
                85                  90                  95

Ile Asp Ser Trp Asn Val
            100

<210> SEQ ID NO 23
<211> LENGTH: 1053
<212> TYPE: DNA
<213> ORGANISM: Streptococcus pyogenes

<400> SEQUENCE: 23
atgccttact acactatttc aaaagtcttt ccttcagata aaacgacaat ggctagtgta      60
aagaacctgc ttcatcaaga aggtattcgt ttggatgctc atttagatta tacttgtgcc     120
atcatgaatg cgcaaaatga tgtgattgct accggttctt actttggaaa tagcttgcgc     180
tgtctttgcg tatccagtgc ctatcaaggt gaaggactte ttaataggat tgtgagtcat     240
ctcattgatg aagaatatgc ccttggcaac tatcatcttt ttgtttatac gaagacctct     300
tctgctgctt ttttcaaaga tcttggtttt actgaaattg tccatatcga caatcacatc     360
agtttcttgg aaaataaaaa aactggtttt caagattatc tgatgacact taataagcct     420
gagcaaacac ctggtaaagt cgctgctatt gttatcaacg ctaaccccett taccttaggg     480 catcaattt tagtagagaa agctgcaaga gaaaatgatt gggttcatct gtttatggtc      540
agtgaagacc gcagtctaat tccttttteg gtgagaaaga ggttgattca agaaggtcta     600
gctcatcttg ataatgtcat atatcatgaa acaggtcctt atttgattag ccaagcgact     660
ttcccagcct atttccaaaa agaagacaat gacgtgatta agagccaagc tttgctggat     720
actgctattt ttctaaagat tgctcaaacc ttacagatta caaaaagata cgttggagaa     780
gagccaacca gccgagtaac tgctatttac aatgaaatta tggcagagca gttgcagcaa     840
gctggtatcc tcctagatat tttgccaagg aaagctatca atcagcagca agatcctatc     900
agtgcctcaa cggctaggca ggcattgaaa gataatgatt gggaccttct ggcaaaactc     960
cttcccaaaa cgtctttaga ttattttgt tcgctaaaag cccaacccat tattaaaaag    1020
atacaagcca cttcatctgt caaacattac taa                                 1053

<210> SEQ ID NO 24
<211> LENGTH: 350
<212> TYPE: PRT
<213> ORGANISM: Streptococcus pyogenes

<400> SEQUENCE: 24

Met Pro Tyr Tyr Thr Ile Ser Lys Val Phe Pro Ser Asp Lys Thr Thr
1               5                   10                  15

Met Ala Ser Val Lys Asn Leu Leu His Gln Glu Gly Ile Arg Leu Asp
                20                  25                  30

Ala His Leu Asp Tyr Thr Cys Ala Ile Met Asn Ala Gln Asn Asp Val
                35                  40                  45

Ile Ala Thr Gly Ser Tyr Phe Gly Asn Ser Leu Arg Cys Leu Cys Val
50                  55                  60

-continued

| | | | | | | | | | | | | | | | |
|---|---|---|---|---|---|---|---|---|---|---|---|---|---|---|---|
|Ser|Ser|Ala|Tyr|Gln|Gly|Glu|Gly|Leu|Leu|Asn|Arg|Ile|Val|Ser|His|
|65| | | | |70| | | |75| | | | |80| |

Leu Ile Asp Glu Glu Tyr Ala Leu Gly Asn Tyr His Leu Phe Val Tyr
                85                    90                    95

Thr Lys Thr Ser Ser Ala Ala Phe Phe Lys Asp Leu Gly Phe Thr Glu
              100                 105                110

Ile Val His Ile Asp Asn His Ile Ser Phe Leu Glu Asn Lys Lys Thr
            115               120               125

Gly Phe Gln Asp Tyr Leu Met Thr Leu Asn Lys Pro Glu Gln Thr Pro
        130               135               140

Gly Lys Val Ala Ala Ile Val Ile Asn Ala Asn Pro Phe Thr Leu Gly
145                 150               155              160

His Gln Phe Leu Val Glu Lys Ala Ala Arg Glu Asn Asp Trp Val His
            165             170               175

Leu Phe Met Val Ser Glu Asp Arg Ser Leu Ile Pro Phe Ser Val Arg
        180               185               190

Lys Arg Leu Ile Gln Glu Gly Leu Ala His Leu Asp Asn Val Ile Tyr
            195             200               205

His Glu Thr Gly Pro Tyr Leu Ile Ser Gln Ala Thr Phe Pro Ala Tyr
        210               215               220

Phe Gln Lys Glu Asp Asn Asp Val Ile Lys Ser Gln Ala Leu Leu Asp
225                 230               235              240

Thr Ala Ile Phe Leu Lys Ile Ala Gln Thr Leu Gln Ile Thr Lys Arg
            245             250               255

Tyr Val Gly Glu Glu Pro Thr Ser Arg Val Thr Ala Ile Tyr Asn Glu
        260               265               270

Ile Met Ala Glu Gln Leu Gln Gln Ala Gly Ile Leu Leu Asp Ile Leu
            275             280               285

Pro Arg Lys Ala Ile Asn Gln Gln Gln Asp Pro Ile Ser Ala Ser Thr
        290               295               300

Ala Arg Gln Ala Leu Lys Asp Asn Asp Trp Asp Leu Leu Ala Lys Leu
305                 310               315              320

Leu Pro Lys Thr Ser Leu Asp Tyr Phe Cys Ser Leu Lys Ala Gln Pro
            325             330               335

Ile Ile Lys Lys Ile Gln Ala Thr Ser Ser Val Lys His Tyr
        340               345               350

<210> SEQ ID NO 25
<211> LENGTH: 642
<212> TYPE: DNA
<213> ORGANISM: Streptococcus pyogenes

<400> SEQUENCE: 25
atggtgataa ggttgttgct cttattgaat accgtgacgg tagcctcatg gatgtggttt    60
acaatgtgta agacactta ttttcaggc gaagctatcc aacttagtga tatgttaaga   120
gcccgcgaag aaagagctct gcgtcagctg catttattaa aggagtaccc agaaggtagc   180
ttattatcgg tcaccatgaa tatccctgga ccaattaaaa cctctcctaa acttcttgaa   240
gcttttgata tagtgattaa ggccattcaa actgccttag ctgacgataa gatttgttac   300
cagttgcgat tactgcctac aacgggttat gagtattacc tcatcacaag tctacctagc   360
cgcgacctga agttaaaaat gatagcctta gagacagagt tgccaatagg tcgtctcatg   420
gatttagatg tcttggtctt gcaaaatgat ctgcctcatt caattagcag aaccgtatta   480
ggaggctccc ctaggcaatg ttttatctgt tctaaagagg ccaaagtctg cggtcgccta   540

```
cgtaagcaca gtgtcgagga gatgcagact gctatttcaa aattactcca ttcattttc    600 aataaagaca accaatcatc gtcatcagat aagacaggtt ga                      642
```

<210> SEQ ID NO 26
<211> LENGTH: 213
<212> TYPE: PRT
<213> ORGANISM: Streptococcus pyogenes

<400> SEQUENCE: 26

```
Met Val Ile Arg Leu Leu Leu Leu Asn Thr Val Thr Val Ala Ser
1               5                   10                  15

Trp Met Trp Phe Thr Met Cys Lys Asp Thr Tyr Phe Ser Gly Glu Ala
            20                  25                  30

Ile Gln Leu Ser Asp Met Leu Arg Ala Arg Glu Arg Ala Leu Arg
        35                  40                  45

Gln Leu His Leu Leu Lys Glu Tyr Pro Glu Gly Ser Leu Leu Ser Val
    50                  55                  60

Thr Met Asn Ile Pro Gly Pro Ile Lys Thr Ser Pro Lys Leu Leu Glu
65                  70                  75                  80

Ala Phe Asp Ile Val Ile Lys Ala Ile Gln Thr Ala Leu Ala Asp Asp
                85                  90                  95

Lys Ile Cys Tyr Gln Leu Arg Leu Leu Pro Thr Thr Gly Tyr Glu Tyr
            100                 105                 110

Tyr Leu Ile Thr Ser Leu Pro Ser Arg Asp Leu Lys Leu Lys Met Ile
        115                 120                 125

Ala Leu Glu Thr Glu Leu Pro Ile Gly Arg Leu Met Asp Leu Asp Val
    130                 135                 140

Leu Val Leu Gln Asn Asp Leu Pro His Ser Ile Ser Arg Thr Val Leu
145                 150                 155                 160

Gly Gly Ser Pro Arg Gln Cys Phe Ile Cys Ser Lys Glu Ala Lys Val
                165                 170                 175

Cys Gly Arg Leu Arg Lys His Ser Val Glu Glu Met Gln Thr Ala Ile
            180                 185                 190

Ser Lys Leu Leu His Ser Phe Phe Asn Lys Asp Asn Gln Ser Ser Ser
        195                 200                 205

Ser Asp Lys Thr Gly
    210
```

<210> SEQ ID NO 27
<211> LENGTH: 1395
<212> TYPE: DNA
<213> ORGANISM: Streptococcus pyogenes

<400> SEQUENCE: 27

```
atgacgaaaa tccgtataac ggaaacagtt ttacgtgatg gtcaacaaag tcagattgcc    60
acacgtatga caaccaagga aatgattcct attctcgaaa cgctagacaa tgctggttat   120
catgcccttg aaatgtgggg aggagcaacc tttgattcct gcctacgctt tttaaatgaa   180
gacccttggg aacggctaag agccatccgt aaagcagtga aaaagactaa acttcagatg   240
ctcttacgcg acaaaaacct tcttggatat cgcaattatg ctgacgatgt ggtcagatcc   300
tttattcaaa atccattga aaatgggatt gatattgtcc gtattttcga tgctttaaac   360
gacccacgca acttgcaaac agctgtttca gcgactaaaa aatttggagg catgctcaa    420 gttgccattt cttacacgac aagtccggta cataccattg actactttgt tgaattggcg   480
```

-continued

```
aaagcttacc aagctatcgg agcggactcc atttgtatca agacatggc tggtgtctta      540 actcctgaaa taggttacca attggtcaaa tgtatcaagg agaatacaac tatccctctt      600
gaggttcata cccatgctac cagtggtatt tcagaaatga cttacttaaa agtagcagaa      660
gcaggagctg atattattga tacggcgatt tcctcttttt caggggggaac cagtcagcct      720 gccacagagt caatggcgat tgccttgacg gatttaggct ttgacacagg cttggatatg      780
caagaggtgg ccaaagttgc agaatatttc aacactattc gtgaccacta tcgagaaata      840 gggatttttaa atcctaaagt caaagatact gagccaaaaa cattgattta ccaagttcca      900
ggtggcatgc tatcaaacct attgagccaa ttaaccgagc aaggcctaac tgataaatac      960
gaagaagtct tagcagaagt acctaaagta agggctgatc ttgggtatcc gccactcgta     1020
acgccattat cacaaatggt tggcacacag gccttgatga atatcatctc aggggaacgt     1080
tacaaggtag ttccaaatga aatcaaagac tatgttcgag ggctatacgg tcaatcacca     1140
gcgccattag cagaaggtat caagagaaa atcattggtg acgaagcagt tattacttgc     1200
agaccagccg acctaatcga gcctcaaatg atttatctac gtgacgagat tgctccatac     1260
gctcattcag aagaagacgt gttaagctat gcaagcttcc cgcaacaagc tagagatttc     1320
ttgggacgcc gtgaagatcc tttctatgat gttccggttc aagaagttac tgtacaactg     1380
gacattcaag actaa                                                     1395
```

<210> SEQ ID NO 28
<211> LENGTH: 464
<212> TYPE: PRT
<213> ORGANISM: Streptococcus pyogenes

<400> SEQUENCE: 28

```
Met Thr Lys Ile Arg Ile Thr Glu Thr Val Leu Arg Asp Gly Gln Gln
1               5                   10                  15

Ser Gln Ile Ala Thr Arg Met Thr Thr Lys Glu Met Ile Pro Ile Leu
            20                  25                  30

Glu Thr Leu Asp Asn Ala Gly Tyr His Ala Leu Glu Met Trp Gly Gly
        35                  40                  45

Ala Thr Phe Asp Ser Cys Leu Arg Phe Leu Asn Glu Asp Pro Trp Glu
    50                  55                  60

Arg Leu Arg Ala Ile Arg Lys Ala Val Lys Lys Thr Lys Leu Gln Met
65                  70                  75                  80

Leu Leu Arg Gly Gln Asn Leu Leu Gly Tyr Arg Asn Tyr Ala Asp Asp
                85                  90                  95

Val Val Arg Ser Phe Ile Gln Lys Ser Ile Glu Asn Gly Ile Asp Ile
            100                 105                 110

Val Arg Ile Phe Asp Ala Leu Asn Asp Pro Arg Asn Leu Gln Thr Ala
        115                 120                 125

Val Ser Ala Thr Lys Lys Phe Gly Gly His Ala Gln Val Ala Ile Ser
    130                 135                 140

Tyr Thr Thr Ser Pro Val His Thr Ile Asp Tyr Phe Val Glu Leu Ala
145                 150                 155                 160

Lys Ala Tyr Gln Ala Ile Gly Ala Asp Ser Ile Cys Ile Lys Asp Met
                165                 170                 175

Ala Gly Val Leu Thr Pro Glu Ile Gly Tyr Gln Leu Val Lys Cys Ile
            180                 185                 190

Lys Glu Asn Thr Thr Ile Pro Leu Glu Val His Thr His Ala Thr Ser
        195                 200                 205
```

```
Gly Ile Ser Glu Met Thr Tyr Leu Lys Val Ala Glu Ala Gly Ala Asp
    210                 215                 220

Ile Ile Asp Thr Ala Ile Ser Ser Phe Ser Gly Gly Thr Ser Gln Pro
225                 230                 235                 240

Ala Thr Glu Ser Met Ala Ile Ala Leu Thr Asp Leu Gly Phe Asp Thr
                245                 250                 255

Gly Leu Asp Met Gln Glu Val Ala Lys Val Ala Glu Tyr Phe Asn Thr
            260                 265                 270

Ile Arg Asp His Tyr Arg Glu Ile Gly Ile Leu Asn Pro Lys Val Lys
        275                 280                 285

Asp Thr Glu Pro Lys Thr Leu Ile Tyr Gln Val Pro Gly Gly Met Leu
290                 295                 300

Ser Asn Leu Leu Ser Gln Leu Thr Glu Gln Gly Leu Thr Asp Lys Tyr
305                 310                 315                 320

Glu Glu Val Leu Ala Glu Val Pro Lys Val Arg Ala Asp Leu Gly Tyr
                325                 330                 335

Pro Pro Leu Val Thr Pro Leu Ser Gln Met Val Gly Thr Gln Ala Leu
            340                 345                 350

Met Asn Ile Ile Ser Gly Glu Arg Tyr Lys Val Val Pro Asn Glu Ile
        355                 360                 365

Lys Asp Tyr Val Arg Gly Leu Tyr Gly Gln Ser Pro Ala Pro Leu Ala
370                 375                 380

Glu Gly Ile Lys Glu Lys Ile Ile Gly Asp Glu Ala Val Ile Thr Cys
385                 390                 395                 400

Arg Pro Ala Asp Leu Ile Glu Pro Gln Met Ile Tyr Leu Arg Asp Glu
                405                 410                 415

Ile Ala Pro Tyr Ala His Ser Glu Glu Asp Val Leu Ser Tyr Ala Ser
            420                 425                 430

Phe Pro Gln Gln Ala Arg Asp Phe Leu Gly Arg Arg Glu Asp Pro Phe
        435                 440                 445

Tyr Asp Val Pro Val Gln Glu Val Thr Val Gln Leu Asp Ile Gln Asp
450                 455                 460
```

<210> SEQ ID NO 29
<211> LENGTH: 1224
<212> TYPE: DNA
<213> ORGANISM: Streptococcus pyogenes

<400> SEQUENCE: 29

```
atgacgaatt taacgtttta tgcaaaaatc ggtatttcag aagaagagca tgactctttt      60
gttaaagaac atcagcaaat tagcgtttta caaggtagtg attgggcaaa aatcaaaaat     120
caatggcaga atgagcgaat tggtatctat aaagaggaaa agcaggttgc ctctttatca     180
cttttgatta agctattgcc acttggaaga agcattattt atattccaag agggccagtc     240
atggattatc ttgaccgtga tttggtggca tttaccatga aaacactaaa ggattatggt     300
aaaactaaaa aggccctctt tatcaaatat gatccagcta tcctgttaaa acaatacgca     360
ctgggacagg aagaagaaga aaaacccttta gctttagcag ctattaagaa tctccaagaa     420
gctggtgttc attggactgg tttaacaatg gagattgcag atagtatcca acctcgtttc     480
caagctaata tttacactca agaaaacctt gagatgcaat tcctaagca taccagacgt     540
ttaataaaag atgctaagca gcgtggtgta aaaacatatc gtgtcagtca atcagaactt     600
cacaaatttt ccaagattgt ctccttaaca gaaaaacgta aaatatttc tttgcgtaac     660
gaagcttact ttcaaaagtt gatgactact tatggggata aggcctactt acatctagca     720
```

```
aaagtgaata ttcctcaaaa actagatcaa taccgccagc aattaattct tattaaccaa    780
gatattactc gcacccaagc tcatcaaaag aagcgtttaa aaaaattaga agatcaaaaa    840
gcttctttag aacgttatat aactgaattt gaaggcttta cagaccaata tcctgaggaa    900
gttgttgtag caggtatatt atctatttct tatggaaatg ttatggaaat gctttatgct    960
gggatgaatg atgattttaa gaagttttat cctcagtatc tgctgtatcc taatgttttt   1020
caggatgctt atcaagatgg tattatttgg gctaacatgg gaggagtaga aggctcgctt   1080
gatgatggac ttaccaaatt taaggccaac tttgctccga caatagaaga atttatagga   1140
gaatttaatc tccctgtcag cccacttat catattgcta ataccatgta caaaatacga   1200
aaacagttaa agaataaaca ttaa                                          1224
```

<210> SEQ ID NO 30
<211> LENGTH: 407
<212> TYPE: PRT
<213> ORGANISM: Streptococcus pyogenes

<400> SEQUENCE: 30

```
Met Thr Asn Leu Thr Phe Tyr Ala Lys Ile Gly Ile Ser Glu Glu Glu
1               5                   10                  15

His Asp Ser Phe Val Lys Glu His Gln Gln Ile Ser Val Leu Gln Gly
            20                  25                  30

Ser Asp Trp Ala Lys Ile Lys Asn Gln Trp Gln Asn Glu Arg Ile Gly
        35                  40                  45

Ile Tyr Lys Glu Glu Lys Gln Val Ala Ser Leu Ser Leu Leu Ile Lys
    50                  55                  60

Leu Leu Pro Leu Gly Arg Ser Ile Ile Tyr Ile Pro Arg Gly Pro Val
65                  70                  75                  80

Met Asp Tyr Leu Asp Arg Asp Leu Val Ala Phe Thr Met Lys Thr Leu
                85                  90                  95

Lys Asp Tyr Gly Lys Thr Lys Lys Ala Leu Phe Ile Lys Tyr Asp Pro
            100                 105                 110

Ala Ile Leu Leu Lys Gln Tyr Ala Leu Gly Glu Glu Glu Glu Lys
        115                 120                 125

Pro Leu Ala Leu Ala Ala Ile Lys Asn Leu Gln Glu Ala Gly Val His
    130                 135                 140

Trp Thr Gly Leu Thr Met Glu Ile Ala Asp Ser Ile Gln Pro Arg Phe
145                 150                 155                 160

Gln Ala Asn Ile Tyr Thr Gln Glu Asn Leu Glu Met Gln Phe Pro Lys
                165                 170                 175

His Thr Arg Arg Leu Ile Lys Asp Ala Lys Gln Arg Gly Val Lys Thr
            180                 185                 190

Tyr Arg Val Ser Gln Ser Glu Leu His Lys Phe Ser Lys Ile Val Ser
        195                 200                 205

Leu Thr Glu Lys Arg Lys Asn Ile Ser Leu Arg Asn Glu Ala Tyr Phe
    210                 215                 220

Gln Lys Leu Met Thr Thr Tyr Gly Asp Lys Ala Tyr Leu His Leu Ala
225                 230                 235                 240

Lys Val Asn Ile Pro Gln Lys Leu Asp Gln Tyr Arg Gln Gln Leu Ile
                245                 250                 255

Leu Ile Asn Gln Asp Ile Thr Arg Thr Gln Ala His Gln Lys Lys Arg
            260                 265                 270

Leu Lys Lys Leu Glu Asp Gln Lys Ala Ser Leu Glu Arg Tyr Ile Thr
```

-continued

```
            275                 280                 285
Glu Phe Glu Gly Phe Thr Asp Gln Tyr Pro Glu Val Val Ala
    290                 295                 300

Gly Ile Leu Ser Ile Ser Tyr Gly Asn Val Met Glu Met Leu Tyr Ala
305                 310                 315                 320

Gly Met Asn Asp Asp Phe Lys Lys Phe Tyr Pro Gln Tyr Leu Leu Tyr
                325                 330                 335

Pro Asn Val Phe Gln Asp Ala Tyr Gln Asp Gly Ile Ile Trp Ala Asn
                340                 345                 350

Met Gly Gly Val Glu Gly Ser Leu Asp Asp Gly Leu Thr Lys Phe Lys
            355                 360                 365

Ala Asn Phe Ala Pro Thr Ile Glu Glu Phe Ile Gly Glu Phe Asn Leu
    370                 375                 380

Pro Val Ser Pro Leu Tyr His Ile Ala Asn Thr Met Tyr Lys Ile Arg
385                 390                 395                 400

Lys Gln Leu Lys Asn Lys His
                405

<210> SEQ ID NO 31
<211> LENGTH: 483
<212> TYPE: DNA
<213> ORGANISM: Streptococcus pyogenes

<400> SEQUENCE: 31
atgccaaaga gaataagaaa agctctagga gtagttggga aactgatgtc aattgttcct      60
gacactactg aaattattgg aaaaacgatt gataacagtc gaccaattat cgaaaaacgt     120
atggaacaaa acatgaaaa agagatgcaa ttacgcacga taaatgatgt gattaatctt     180
cctgttgatc aggcacaagc tcatttggaa caacttggct ttgtagtagc cactatacct     240
gctaagcctc ataaaaaatg gcttcatagt aatctcaatg aagtggttgc tatgtctcca     300
aaatctggta aatataagat aggaagcctg atcaaactct actacattac tgttgatgtt     360
ttggaaaaaa gtcaagactt attagaccaa gaaaacttgc ggactgtgga acgcaatcaa     420
aaaatcgctg atacttttga gtctgtcaaa cacattcgat ttccttttaa aaaatggcgt     480
taa                                                                   483

<210> SEQ ID NO 32
<211> LENGTH: 160
<212> TYPE: PRT
<213> ORGANISM: Streptococcus pyogenes

<400> SEQUENCE: 32

Met Pro Lys Arg Ile Arg Lys Ala Leu Gly Val Val Gly Lys Leu Met
1               5                   10                  15

Ser Ile Val Pro Asp Thr Thr Glu Ile Ile Gly Lys Thr Ile Asp Asn
            20                  25                  30

Ser Arg Pro Ile Ile Glu Lys Arg Met Glu Gln Lys His Glu Lys Glu
        35                  40                  45

Met Gln Leu Arg Thr Ile Asn Asp Val Ile Asn Leu Pro Val Asp Gln
    50                  55                  60

Ala Gln Ala His Leu Glu Gln Leu Gly Phe Val Val Ala Thr Ile Pro
65                  70                  75                  80

Ala Lys Pro His Lys Lys Trp Leu His Ser Asn Leu Asn Glu Val Val
                85                  90                  95

Ala Met Ser Pro Lys Ser Gly Lys Tyr Lys Ile Gly Ser Leu Ile Lys
```

```
                100             105             110
Leu Tyr Tyr Ile Thr Val Asp Val Leu Glu Lys Ser Gln Asp Leu Leu
            115                 120                 125

Asp Gln Glu Asn Leu Arg Thr Val Glu Arg Asn Gln Lys Ile Ala Asp
    130                 135                 140

Thr Phe Glu Ser Val Lys His Ile Arg Phe Pro Phe Lys Lys Trp Arg
145                 150                 155                 160
```

<210> SEQ ID NO 33
<211> LENGTH: 1345
<212> TYPE: DNA
<213> ORGANISM: Streptococcus pyogenes

<400> SEQUENCE: 33

```
atgatgttaa cgaagggca  acttccctat agtgctgctt ttacaacagg agggctcttt    60
tactttgtta tcattgcatt aagttattat ttgggatcga cactttggct agtctttgtt   120
caggtgtttt gttttactt  atctggttta tatctttata aactcattaa ttatatgaca   180
ggctttcaaa agtggcttt  aacttttca  attagctact atttattatc tgttagtctt   240
ggttttgggg gattgtatcc tactcaactg gctatgccat ttatattaat atcggcttgg   300
tttttaacta agtattttgc ctgtttagtg aaagatgagg cattattct  ttttggcttt   360
gtaggtgctc ttgcaatgct aattgacccg agtacccta  tcttttggtc ttttgcttgt   420
gtgacagttt tttcttataa tataagccaa aagcatcttg caagaggttt ttatcaactg   480
ctagcttcga ttttttggaat gattttagtt ttttacacag caggatattt cattttgaac   540
ttacaagtgc taaatcctta tttatcacaa acgatgattt atccttttac ttttttttaaa   600
tcaggaaact tatcgttgct tttttggactg gctattcagt tgttcttcgc tttggggctt   660
ggtctttga  cgggaatgga gaatgtcatt aggcgattta aaaacaattc tgatagggtc   720
gtcaagtggc tatttgtcat ggtcattcta gaatctatac ttgtggctat attttcacaa   780
gactatcgcc cctatcatct tttacctctt ttacctttg  gattaatttt gactgctatt   840
cctgttggct atcagtatgg tataggatta ggtcagagta gtcatcgcag acgtcatggt   900
aaaaatggtg ttggtcgagt aatgatgatt tatcttaaga gacacttta  tttgccaatt   960
ttaattgtag ggacaatact aatctgttct acttattgtt tcattagtag tattcctctt  1020
aatcaggagc gtgatcatat tgctagttat ttagaacaga actaaataa  aactcaatct  1080
atttatgttt gggatgatac ttctaaaatt tatttggaca gtaaagctaa atctgtttct  1140
caattttagtt ctcctgacat caatacgcaa aaagagagtc atcgaaaaat attagaagat  1200
gaactattag aaaataaggc tgcttatatc gttgttaatc gctataaaaa cctgcctaaa  1260
atcattcaaa aagtattatc tactaattac aaagtagata acagataac  gacaaaaagt  1320
tttattgttt atcagaaaaa gtaat                                         1345
```

<210> SEQ ID NO 34
<211> LENGTH: 447
<212> TYPE: PRT
<213> ORGANISM: Streptococcus pyogenes

<400> SEQUENCE: 34

```
Met Met Leu Thr Lys Gly Gln Leu Pro Tyr Ser Ala Ala Phe Thr Thr
1               5                   10                  15

Gly Gly Leu Phe Tyr Phe Val Ile Ile Ala Leu Ser Tyr Tyr Leu Gly
            20                  25                  30
```

```
Ser Thr Leu Trp Leu Val Phe Val Gln Val Phe Cys Phe Tyr Leu Ser
            35                  40                  45

Gly Leu Tyr Leu Tyr Lys Leu Ile Asn Tyr Met Thr Gly Phe Gln Lys
        50                  55                  60

Val Ala Leu Thr Phe Ser Ile Ser Tyr Tyr Leu Leu Ser Val Ser Leu
 65                  70                  75                  80

Gly Phe Gly Gly Leu Tyr Pro Thr Gln Leu Ala Met Pro Phe Ile Leu
                85                  90                  95

Ile Ser Ala Trp Phe Leu Thr Lys Tyr Phe Ala Cys Leu Val Lys Asp
               100                 105                 110

Glu Ala Phe Ile Leu Phe Gly Phe Val Gly Ala Leu Ala Met Leu Ile
               115                 120                 125

Asp Pro Ser Thr Leu Ile Phe Trp Ser Phe Ala Cys Val Thr Val Phe
130                 135                 140

Ser Tyr Asn Ile Ser Gln Lys His Leu Ala Arg Gly Phe Tyr Gln Leu
145                 150                 155                 160

Leu Ala Ser Ile Phe Gly Met Ile Leu Val Phe Tyr Thr Ala Gly Tyr
                165                 170                 175

Phe Ile Leu Asn Leu Gln Val Leu Asn Pro Tyr Leu Ser Gln Thr Met
               180                 185                 190

Ile Tyr Pro Phe Thr Phe Phe Lys Ser Gly Asn Leu Ser Leu Leu Phe
       195                 200                 205

Gly Leu Ala Ile Gln Leu Phe Phe Ala Leu Gly Leu Gly Leu Leu Thr
       210                 215                 220

Gly Met Glu Asn Val Ile Arg Arg Phe Lys Asn Asn Ser Asp Arg Val
225                 230                 235                 240

Val Lys Trp Leu Phe Val Met Val Ile Leu Glu Ser Ile Leu Val Ala
                245                 250                 255

Ile Phe Ser Gln Asp Tyr Arg Pro Tyr His Leu Leu Pro Leu Leu Pro
               260                 265                 270

Phe Gly Leu Ile Leu Thr Ala Ile Pro Val Gly Tyr Gln Tyr Gly Ile
       275                 280                 285

Gly Leu Gly Gln Ser Ser His Arg Arg His Gly Lys Asn Gly Val
290                 295                 300

Gly Arg Val Met Met Ile Tyr Leu Lys Arg His Phe Tyr Leu Pro Ile
305                 310                 315                 320

Leu Ile Val Gly Thr Ile Leu Ile Cys Ser Thr Tyr Cys Phe Ile Ser
                325                 330                 335

Ser Ile Pro Leu Asn Gln Glu Arg Asp His Ile Ala Ser Tyr Leu Glu
               340                 345                 350

Gln Lys Leu Asn Lys Thr Gln Ser Ile Tyr Val Trp Asp Asp Thr Ser
       355                 360                 365

Lys Ile Tyr Leu Asp Ser Lys Ala Lys Ser Val Ser Gln Phe Ser Ser
       370                 375                 380

Pro Asp Ile Asn Thr Gln Lys Glu Ser His Arg Lys Ile Leu Glu Asp
385                 390                 395                 400

Glu Leu Leu Glu Asn Lys Ala Ala Tyr Ile Val Val Asn Arg Tyr Lys
                405                 410                 415

Asn Leu Pro Lys Ile Ile Gln Leu Val Leu Ser Thr Asn Tyr Lys Val
               420                 425                 430

Asp Lys Gln Ile Thr Thr Lys Ser Phe Ile Val Tyr Gln Lys Lys
       435                 440                 445
```

<210> SEQ ID NO 35
<211> LENGTH: 618
<212> TYPE: DNA
<213> ORGANISM: Streptococcus pyogenes

<400> SEQUENCE: 35

```
atgattaaag ctcagctaaa gaatctaata aaaacaattc atctcgtaaa agaggctggt      60
ttctccctaa atggttcatt gtacatggag ttattgcatg attttacgca tgatgagtta     120
gtacataacc ctataatcga agtacggtt gatacaattc agtcagttga atttgaaagg      180
gtttctttt catataatgg taaggataat gtaataaacg atataagttt ttcaattaaa      240
gcaggagaga ggttagcaat tgttggtgga atggttctg aaaaagtac gattttcaaa       300
ttagcctgcg gtctttacga taattatgaa ggcaatatat atataaatgg tattaatctt     360
tgttcaatac agaaaaagtc atactacaag agaatatccg cattgttcca agatttttta    420
aagtatgaat tgacactgcg tgaaaatgtt ggattgggtg aattatcaaa gttatatagt    480
gatgagtctt ataatacttc attttttacc acatcatggg attcagagaa tgaactgcga     540
ttggaggata tttatataag atatagtgat ggtaagtttc attttacaac tatcgatgaa    600
tcgattaaac gggattaa                                                   618
```

<210> SEQ ID NO 36
<211> LENGTH: 205
<212> TYPE: PRT
<213> ORGANISM: Streptococcus pyogenes

<400> SEQUENCE: 36

```
Met Ile Lys Ala Gln Leu Lys Asn Leu Ile Lys Thr Ile His Leu Val
1               5                   10                  15

Lys Glu Ala Gly Phe Ser Leu Asn Gly Ser Leu Tyr Met Glu Leu Leu
                20                  25                  30

His Asp Phe Thr His Asp Glu Leu Val His Asn Pro Ile Ile Glu Ser
            35                  40                  45

Thr Val Asp Thr Ile Gln Ser Val Glu Phe Glu Arg Val Ser Phe Ser
        50                  55                  60

Tyr Asn Gly Lys Asp Asn Val Ile Asn Asp Ile Ser Phe Ser Ile Lys
65                  70                  75                  80

Ala Gly Glu Arg Leu Ala Ile Val Gly Gly Asn Gly Ser Gly Lys Ser
                85                  90                  95

Thr Ile Phe Lys Leu Ala Cys Gly Leu Tyr Asp Asn Tyr Glu Gly Asn
            100                 105                 110

Ile Tyr Ile Asn Gly Ile Asn Leu Cys Ser Ile Gln Lys Lys Ser Tyr
        115                 120                 125

Tyr Lys Arg Ile Ser Ala Leu Phe Gln Asp Phe Leu Lys Tyr Glu Leu
    130                 135                 140

Thr Leu Arg Glu Asn Val Gly Leu Gly Glu Leu Ser Lys Leu Tyr Ser
145                 150                 155                 160

Asp Glu Ser Tyr Asn Thr Ser Phe Phe Thr Thr Ser Trp Asp Ser Glu
                165                 170                 175

Asn Glu Leu Arg Leu Glu Asp Ile Tyr Ile Arg Tyr Ser Asp Gly Lys
            180                 185                 190

Phe His Phe Thr Thr Ile Asp Glu Ser Ile Lys Arg Asp
        195                 200                 205
```

<210> SEQ ID NO 37
<211> LENGTH: 1434

-continued

```
<212> TYPE: DNA
<213> ORGANISM: Streptococcus pyogenes

<400> SEQUENCE: 37
atgctaagaa aaagagaat tttgggttta tttcgacttg ttgaattaat tttcctagga      60
ttattgttga gtttagttgt ttcgtacctt gcgtggacca atagttttgc aacacttcat    120
aatatattag caactgtcgg aatagtggaa cgaagcaaag atcaacagcc tcgctatcac    180
attggacaag ctattcaagt acaaaaaagt ggtccatatc atcaatggat tggaactatt    240
aataaacagg tagaagatat agccgaaaat taccgagtga gttatcatta tgaagtggta    300
tttccaatag gaaaagtcac tgtttctttg ccagaacata acctgaaaga gcctgataaa    360
ccgaggttta aaaaggaga tatcgttaaa ttatcttcat taactaaaaa gccacatata    420
aaagtatatc aaggtcaatt agcgactatt aaacaagtta aaaaatgcta tgactattcg    480
ttaggaggat atcagtacga tattaatctg aaagataatc taagattaga tggaatttca    540
gagcaagatt ttgttaaacc ttattatatt aggttcaata aaggaaattc ccctgagcaa    600
aacaatcgtc ttttgcgaaa agctttcgct tatgcaaagc agcatccaaa tagcgttata    660
tcttttccaa agggcaatt tcacattggc tctttgcctt cacaaaaaga ttattttgag    720
cttccatctg atacagctat tattggtcat cagacagagt tcattattca cggtaaaatg    780
ttgtggtttg gattccctac aggaccaaag gctgaacaag gtgttcgtaa tctcgtgttg    840
actggagtgc atttcaaagc aaatgatttg aaaaaaggag accactttat gattatggct    900
gatcatggta ctgattggca tatttacgat aacaaattta ctatggttca taagcgtaat    960
agtcatattt ttgatttagg atctctacaa aattcattgt ttgagaaaaa ccaatttatt   1020
ggctatgcgc cagaattagt acaagaccaa cagctgctat caaaggctca agggcatgat   1080
ttttttttcag aagtcattca gtttgatgct gctgttcatc attttgcatg ggatggaggt   1140
ctacttagta atattgctcc aaactatgaa gcatttaacc aaactcgaca tctatgtcac   1200
aatattactg taagccaaaa tcaattttta ccttatatag atccgactgg ttgcctgaga   1260
gcctatagtg gttctattgg tcagcattcc tcaaaagtag gagttattag ggttttaaat   1320
aatgtttta cctcatccat tgttactaaa gcgaagctca ctagttggtt tatggaacct   1380
attcattttc caccaaattc accggttatt gtcgcaggta atatcattaa ttga         1434

<210> SEQ ID NO 38
<211> LENGTH: 477
<212> TYPE: PRT
<213> ORGANISM: Streptococcus pyogenes

<400> SEQUENCE: 38

Met Leu Arg Lys Lys Arg Ile Leu Gly Leu Phe Arg Leu Val Glu Leu
1               5                   10                  15

Ile Phe Leu Gly Leu Leu Leu Ser Leu Val Ser Tyr Leu Ala Trp
            20                  25                  30

Thr Asn Ser Phe Ala Thr Leu His Asn Ile Leu Ala Thr Val Gly Ile
        35                  40                  45

Val Glu Arg Ser Lys Asp Gln Gln Pro Arg Tyr His Ile Gly Gln Ala
    50                  55                  60

Ile Gln Val Gln Lys Ser Gly Pro Tyr His Gln Trp Ile Gly Thr Ile
65                  70                  75                  80

Asn Lys Gln Val Glu Asp Ile Ala Glu Asn Tyr Arg Val Ser Tyr His
                85                  90                  95
```

```
Tyr Glu Val Val Phe Pro Ile Gly Lys Val Thr Val Ser Leu Pro Glu
            100                 105                 110

His Asn Leu Lys Glu Pro Asp Lys Pro Arg Phe Lys Lys Gly Asp Ile
        115                 120                 125

Val Lys Leu Ser Ser Leu Thr Lys Lys Pro His Ile Lys Val Tyr Gln
    130                 135                 140

Gly Gln Leu Ala Thr Ile Lys Gln Val Lys Lys Cys Tyr Asp Tyr Ser
145                 150                 155                 160

Leu Gly Gly Tyr Gln Tyr Asp Ile Asn Leu Lys Asp Asn Leu Arg Leu
                165                 170                 175

Asp Gly Ile Ser Glu Gln Asp Phe Val Lys Pro Tyr Tyr Ile Arg Phe
            180                 185                 190

Asn Lys Gly Asn Ser Pro Glu Gln Asn Asn Arg Leu Leu Arg Lys Ala
        195                 200                 205

Phe Ala Tyr Ala Lys Gln His Pro Asn Ser Val Ile Ser Phe Pro Lys
    210                 215                 220

Gly Gln Phe His Ile Gly Ser Leu Pro Ser Gln Lys Asp Tyr Phe Glu
225                 230                 235                 240

Leu Pro Ser Asp Thr Ala Ile Ile Gly His Gln Thr Glu Phe Ile Ile
                245                 250                 255

His Gly Lys Met Leu Trp Phe Gly Phe Pro Thr Gly Pro Lys Ala Glu
            260                 265                 270

Gln Gly Val Arg Asn Leu Val Leu Thr Gly Val His Phe Lys Ala Asn
        275                 280                 285

Asp Leu Lys Lys Gly Asp His Phe Met Ile Met Ala Asp His Gly Thr
    290                 295                 300

Asp Trp His Ile Tyr Asp Asn Lys Phe Thr Met Val His Lys Arg Asn
305                 310                 315                 320

Ser His Ile Phe Asp Leu Gly Ser Leu Gln Asn Ser Leu Phe Glu Lys
                325                 330                 335

Asn Gln Phe Ile Gly Tyr Ala Pro Glu Leu Val Gln Asp Gln Gln Leu
            340                 345                 350

Leu Ser Lys Ala Gln Gly His Asp Phe Ser Glu Val Ile Gln Phe
        355                 360                 365

Asp Ala Ala Val His His Phe Ala Trp Asp Gly Gly Leu Leu Ser Asn
    370                 375                 380

Ile Ala Pro Asn Tyr Glu Ala Phe Asn Gln Thr Arg His Leu Cys His
385                 390                 395                 400

Asn Ile Thr Val Ser Gln Asn Gln Phe Leu Pro Tyr Ile Asp Pro Thr
                405                 410                 415

Gly Cys Leu Arg Ala Tyr Ser Gly Ser Ile Gly Gln His Ser Ser Lys
            420                 425                 430

Val Gly Val Ile Arg Val Leu Asn Asn Val Phe Thr Ser Ser Ile Val
        435                 440                 445

Thr Lys Ala Lys Leu Thr Ser Trp Phe Met Glu Pro Ile His Phe Pro
    450                 455                 460

Pro Asn Ser Pro Val Ile Val Ala Gly Asn Ile Ile Asn
465                 470                 475
```

<210> SEQ ID NO 39
<211> LENGTH: 1020
<212> TYPE: DNA
<213> ORGANISM: Streptococcus pyogenes

<400> SEQUENCE: 39

-continued

```
atgtcaactc acttaagaaa acttccaggg ctgttacttt gcttattgtt agctcttcca      60
gcctggtgtt tagggcgctt atttcccatt attggagcac ctgttttttgc tattctttta   120
ggaatgttgt tagccttgtt ttatgaacat cgtgacaaga ctaaagaggg aattagtttt    180
acatccaagt atattttaca aacagcagtg gttttgcttg gttttggatt aaacctaacc    240
caagttatgg cagtgggcat gcagtcttta ccgattatca tttcaactat tgcgacagct    300
cttttggtag cttatggctt acagaaatgg ctgcgcttag atgtcaatac agccaccttg    360
gtaggtgtag gatcttccat tgtgggggg tctgctgttg cagcgacagc tcctgtcatt     420
aaggcaaagg atgacgaggt tgctaaggca atttcagtca tttttctctt taatatgtta   480
gcagctttgc tatttccaag tttaggacaa ttactaggct tatctaatga aggttttgct    540
attttgtccg ggacagctgt taacgacact tcttccgtga ctgcaacggc cacggcctgg   600
gatgcccttc accattccaa tacactagat ggagcaacca ttgttaaatt gactcgcacc    660
ttggctattc tcccaattac tttaggttta tcccttacc gagcgaaaaa agagcacgac    720
atcgttacag aagaaaactt tagccttagg aagtcattcc ctcgtttcat cctcttcttt   780
ttattagctt ctctcatcac aacattgatg accagtttgg gagtttctgc cgatagtttc   840
cattacctaa aaaccttatc aaaattcttt atcgtgatgg ctatggcagc gattggttta    900
aacacaaacc tggttaaact gattaagacg ggcggtcagg ctatcctttt aggagctatt   960
tgctgggtag ctatcaccct tgtcagttta gccatgcaat taagtttggg catttggtaa  1020
```

<210> SEQ ID NO 40
<211> LENGTH: 339
<212> TYPE: PRT
<213> ORGANISM: Streptococcus pyogenes

<400> SEQUENCE: 40

```
Met Ser Thr His Leu Arg Lys Leu Pro Gly Leu Leu Cys Leu Leu
 1               5                  10                  15

Leu Ala Leu Pro Ala Trp Cys Leu Gly Arg Leu Phe Pro Ile Ile Gly
            20                  25                  30

Ala Pro Val Phe Ala Ile Leu Leu Gly Met Leu Leu Ala Leu Phe Tyr
        35                  40                  45

Glu His Arg Asp Lys Thr Lys Glu Gly Ile Ser Phe Thr Ser Lys Tyr
    50                  55                  60

Ile Leu Gln Thr Ala Val Val Leu Leu Gly Phe Gly Leu Asn Leu Thr
65                  70                  75                  80

Gln Val Met Ala Val Gly Met Gln Ser Leu Pro Ile Ile Ser Thr
                85                  90                  95

Ile Ala Thr Ala Leu Leu Val Ala Tyr Gly Leu Gln Lys Trp Leu Arg
            100                 105                 110

Leu Asp Val Asn Thr Ala Thr Leu Val Gly Val Gly Ser Ser Ile Cys
        115                 120                 125

Gly Gly Ser Ala Val Ala Ala Thr Ala Pro Val Ile Lys Ala Lys Asp
    130                 135                 140

Asp Glu Val Ala Lys Ala Ile Ser Val Ile Phe Leu Phe Asn Met Leu
145                 150                 155                 160

Ala Ala Leu Leu Phe Pro Ser Leu Gly Gln Leu Leu Gly Leu Ser Asn
                165                 170                 175

Glu Gly Phe Ala Ile Phe Ala Gly Thr Ala Val Asn Asp Thr Ser Ser
            180                 185                 190
```

| | | | | | | | | | | | |
|---|---|---|---|---|---|---|---|---|---|---|---|
|Val|Thr|Ala|Thr|Ala|Thr|Ala|Trp|Asp|Ala|Leu|His|His|Ser|Asn|Thr|
| |195| | | |200| | | |205| | | | | | |

Leu Asp Gly Ala Thr Ile Val Lys Leu Thr Arg Thr Leu Ala Ile Leu
    210             215                 220

Pro Ile Thr Leu Gly Leu Ser Leu Tyr Arg Ala Lys Lys Glu His Asp
225                 230                 235                 240

Ile Val Thr Glu Glu Asn Phe Ser Leu Arg Lys Ser Phe Pro Arg Phe
                245                 250                 255

Ile Leu Phe Phe Leu Leu Ala Ser Leu Ile Thr Thr Leu Met Thr Ser
            260                 265                 270

Leu Gly Val Ser Ala Asp Ser Phe His Tyr Leu Lys Thr Leu Ser Lys
        275                 280                 285

Phe Phe Ile Val Met Ala Met Ala Ala Ile Gly Leu Asn Thr Asn Leu
    290                 295                 300

Val Lys Leu Ile Lys Thr Gly Gly Gln Ala Ile Leu Leu Gly Ala Ile
305                 310                 315                 320

Cys Trp Val Ala Ile Thr Leu Val Ser Leu Ala Met Gln Leu Ser Leu
                325                 330                 335

Gly Ile Trp

<210> SEQ ID NO 41
<211> LENGTH: 2637
<212> TYPE: DNA
<213> ORGANISM: Streptococcus pyogenes

<400> SEQUENCE: 41

```
atgataaaga aaaccttatg gaaggatatt ttgagagcta tcaagaatag taaagggcga    60
ttcatttcct tattttttcct aatggcctta ggctcctttg ctttagttgg acttaaagtc   120
accggtccag atatggaacg aacagccagc cgttacctcg aaagacacca ggtgatggac   180
ctaacggtac tggcttctca tcaatttttcc caagccgata acaagagtt agatacgtta   240
aaagggctc atttagaata tggtcattta cttgatgtca gtctaactag caaccagaaa   300
tctcttaggc tctatagcgt gccaaagaaa gtgtctaagc cagtcttggt taagggagt   360
tggccaaagc gagagacaga tttggtttta tcctcctcac ttgctaaaaa ctatcagatt   420
ggagatgaac tagcagtcac ctcacctatg aaggtttgc tgacgacaac ccattttcaa   480
gtggttggtt ttgcgaattc ttcagaagtt tggtccaagt ccaatttagg aagttcctca   540
accggagatg gaagtctcta cgcttatgct tttgttaatc caaacgtttt taaaagtgcc   600
tttaacctgc tgcgcatccg ttttagtcat cttcgtctga caaacgctttt ttccaaagac   660
tatcaaaaaa gggtaaccca aaaccaagct catttggata atctacttaa agataatggc   720
cagaagcgtt atgatgacct ccaaaatcag tatgaccttg ccttaaaaaa tggcagagca   780
gcacttgcaa aggaaacagt gaaactagct gcgagtgagg agaacttaac tttttttagaa   840
ggctctgctt tacaagaagc taagcatcag attgaacaag caaacaagc attagccaag   900
gaggaaaagc agttagagca ggtgcaggct acaaaagata gctagaaaa acccagttac   960
ctgacttata atcgctcgac cctaccagga ggagaaggat atcatactta tgcaacttca  1020
acgacctcca tttcaaatgt tggaaatatt tttcctgttg ttctttatct cgtagctgct  1080
ctagtagcct ttaccaccat gacacgttat gttgatgaag aaagaacaag ctctggtcta  1140
ttaaaagcca ttggttattc taacaaggat atcagtttaa agtttctat ctatgggctt  1200
ttagccagtt tttagggac aactttaggt attattgggg gaacttacct cttatctacc  1260
```

-continued

```
ttgatttcag agatcttaac aggagctttg actattggaa agactcacct ttatagttat   1320
tggttttata atggcatagc ttacttgctg gctatgttat ctgctgtttt accagcctac   1380
ttaattgtca aaaaggaatt attcctcaat gcagctcagt tattgctgcc caaacctcct   1440
agtaaggggg caaaaatctg gttggaacac cttacttttg tctggaaagc cctgtccttt   1500
actcacaagg tgaccatacg taatattttt cgctataaac aaagaatgct gatgaccatt   1560
gtaggcgttg caggctcagt agcccttttg tttgcaggct tagggattca gtcgtcatta   1620
gccaaagtag ttgagcatca atttggtgat taacgactt atgatatttt ggctgtcggt   1680
tcggccaaag cgacagcgac agagcaaact gacttagcta gctatcttaa caagaacct    1740 attacagggt accaaaaggt atcttatgcc agcttaaccc ttcctgtaaa gggattacct   1800
gataagcaaa gtatttccat tttatcaagt tcagctactt ctcttagtcc ctattttaat   1860
ctgctggata gtcaggagca aaagaaggtt cccattccaa cctctggtgt tttgatttct   1920
gagaaattag cctcctatta caaggtaaaa ccaggtgatc agttggtatt gactgatcgg   1980 aaggacagt cttataaagt gacgattaaa caggttattg acatgacagt tggccattac    2040
ctgataatgt ctgataccta ttttaagaat cattttaaag gattggaggc tgctcctgcc   2100
tatctgatta aggtaaaaga caaagatagc aagcacataa aggagacagc cagtgacttg   2160
ttaaccttaa aagcgattag agcagtttca caaaacgtca atcatattaa atctgttcag   2220
ctagtagtca cctctcttaa tcaggtcatg accctccttg tcttcttgtc tatttttatta  2280 gcaatcgtta tcctttataa cttaacgact attaatattg ctgagcgtat tcgagaatta   2340
tccactatta aagttctggg attttacgat caggaggtca ccttatatat ttatcgagaa   2400
actatttcgc tatccctagt aggcattctt ttaggtatct atttaggaaa aggcctgcat   2460
acttatatca tgacaatgat ttcaactggg gatattcaat ttggtgtaaa ggttgatgct   2520
tatgtttatc tagtgccaat tctagtaatc cttagcttgt tagcggtatt aggtatctgg   2580
gttaatcgcc atttaaaaaa ggttgatatg ttagaagctt tgaaatccat agattga      2637
```

<210> SEQ ID NO 42
<211> LENGTH: 878
<212> TYPE: PRT
<213> ORGANISM: Streptococcus pyogenes

<400> SEQUENCE: 42

```
Met Ile Lys Lys Thr Leu Trp Lys Asp Ile Leu Arg Ala Ile Lys Asn
1               5                   10                  15

Ser Lys Gly Arg Phe Ile Ser Leu Phe Phe Leu Met Ala Leu Gly Ser
            20                  25                  30

Phe Ala Leu Val Gly Leu Lys Val Thr Gly Pro Asp Met Glu Arg Thr
        35                  40                  45

Ala Ser Arg Tyr Leu Glu Arg His Gln Val Met Asp Leu Thr Val Leu
    50                  55                  60

Ala Ser His Gln Phe Ser Gln Ala Asp Lys Gln Glu Leu Asp Thr Leu
65                  70                  75                  80

Lys Gly Ala His Leu Glu Tyr Gly His Leu Asp Val Ser Leu Thr
                85                  90                  95

Ser Asn Gln Lys Ser Leu Arg Leu Tyr Ser Val Pro Lys Lys Val Ser
            100                 105                 110

Lys Pro Val Leu Val Lys Gly Ser Trp Pro Lys Arg Glu Thr Asp Leu
        115                 120                 125

Val Leu Ser Ser Ser Leu Ala Lys Asn Tyr Gln Ile Gly Asp Glu Leu
```

-continued

```
            130                 135                 140
Ala Val Thr Ser Pro Met Glu Gly Leu Leu Thr Thr Thr His Phe Gln
145                 150                 155                 160

Val Val Gly Phe Ala Asn Ser Ser Glu Val Trp Ser Lys Ser Asn Leu
                165                 170                 175

Gly Ser Ser Ser Thr Gly Asp Gly Ser Leu Tyr Ala Tyr Ala Phe Val
                180                 185                 190

Asn Pro Asn Val Phe Lys Ser Ala Phe Asn Leu Leu Arg Ile Arg Phe
                195                 200                 205

Ser His Leu Arg Leu Thr Asn Ala Phe Ser Lys Asp Tyr Gln Lys Arg
    210                 215                 220

Val Thr Gln Asn Gln Ala His Leu Asp Asn Leu Leu Lys Asp Asn Gly
225                 230                 235                 240

Gln Lys Arg Tyr Asp Asp Leu Gln Asn Gln Tyr Asp Leu Ala Leu Lys
                245                 250                 255

Asn Gly Arg Ala Ala Leu Ala Lys Glu Thr Val Lys Leu Ala Ala Ser
                260                 265                 270

Glu Glu Asn Leu Thr Phe Leu Glu Gly Ser Ala Leu Gln Glu Ala Lys
    275                 280                 285

His Gln Ile Glu Gln Gly Lys Gln Ala Leu Ala Lys Glu Glu Lys Gln
    290                 295                 300

Leu Glu Gln Val Gln Ala Thr Lys Asp Lys Leu Glu Lys Pro Ser Tyr
305                 310                 315                 320

Leu Thr Tyr Asn Arg Ser Thr Leu Pro Gly Gly Glu Gly Tyr His Thr
                325                 330                 335

Tyr Ala Thr Ser Thr Thr Ser Ile Ser Asn Val Gly Asn Ile Phe Pro
                340                 345                 350

Val Val Leu Tyr Leu Val Ala Ala Leu Val Ala Phe Thr Thr Met Thr
                355                 360                 365

Arg Tyr Val Asp Glu Glu Arg Thr Ser Ser Gly Leu Leu Lys Ala Ile
    370                 375                 380

Gly Tyr Ser Asn Lys Asp Ile Ser Leu Lys Phe Leu Ile Tyr Gly Leu
385                 390                 395                 400

Leu Ala Ser Phe Leu Gly Thr Thr Leu Gly Ile Ile Gly Gly Thr Tyr
                405                 410                 415

Leu Leu Ser Thr Leu Ile Ser Glu Ile Leu Thr Gly Ala Leu Thr Ile
                420                 425                 430

Gly Lys Thr His Leu Tyr Ser Tyr Trp Phe Tyr Asn Gly Ile Ala Tyr
                435                 440                 445

Leu Leu Ala Met Leu Ser Ala Val Leu Pro Ala Tyr Leu Ile Val Lys
    450                 455                 460

Lys Glu Leu Phe Leu Asn Ala Ala Gln Leu Leu Leu Pro Lys Pro Pro
465                 470                 475                 480

Ser Lys Gly Ala Lys Ile Trp Leu Glu His Leu Thr Phe Val Trp Lys
                485                 490                 495

Ala Leu Ser Phe Thr His Lys Val Thr Ile Arg Asn Ile Phe Arg Tyr
                500                 505                 510

Lys Gln Arg Met Leu Met Thr Ile Val Gly Val Ala Gly Ser Val Ala
                515                 520                 525

Leu Leu Phe Ala Gly Leu Gly Ile Gln Ser Ser Leu Ala Lys Val Val
    530                 535                 540

Glu His Gln Phe Gly Asp Leu Thr Thr Tyr Asp Ile Leu Ala Val Gly
545                 550                 555                 560
```

```
Ser Ala Lys Ala Thr Ala Thr Glu Gln Thr Asp Leu Ala Ser Tyr Leu
            565                 570                 575
Lys Gln Glu Pro Ile Thr Gly Tyr Gln Lys Val Ser Tyr Ala Ser Leu
            580                 585                 590
Thr Leu Pro Val Lys Gly Leu Pro Asp Lys Gln Ser Ile Ser Ile Leu
            595                 600                 605
Ser Ser Ser Ala Thr Ser Leu Ser Pro Tyr Phe Asn Leu Leu Asp Ser
            610                 615                 620
Gln Glu Gln Lys Lys Val Pro Ile Pro Thr Ser Gly Val Leu Ile Ser
625                 630                 635                 640
Glu Lys Leu Ala Ser Tyr Tyr Lys Val Lys Pro Gly Asp Gln Leu Val
            645                 650                 655
Leu Thr Asp Arg Lys Gly Gln Ser Tyr Lys Val Thr Ile Lys Gln Val
            660                 665                 670
Ile Asp Met Thr Val Gly His Tyr Leu Ile Met Ser Asp Thr Tyr Phe
            675                 680                 685
Lys Asn His Phe Lys Gly Leu Glu Ala Ala Pro Ala Tyr Leu Ile Lys
            690                 695                 700
Val Lys Asp Lys Asp Ser Lys His Ile Lys Glu Thr Ala Ser Asp Leu
705                 710                 715                 720
Leu Thr Leu Lys Ala Ile Arg Ala Val Ser Gln Asn Val Asn His Ile
            725                 730                 735
Lys Ser Val Gln Leu Val Val Thr Ser Leu Asn Gln Val Met Thr Leu
            740                 745                 750
Leu Val Phe Leu Ser Ile Leu Leu Ala Ile Val Ile Leu Tyr Asn Leu
            755                 760                 765
Thr Thr Ile Asn Ile Ala Glu Arg Ile Arg Glu Leu Ser Thr Ile Lys
            770                 775                 780
Val Leu Gly Phe Tyr Asp Gln Glu Val Thr Leu Tyr Ile Tyr Arg Glu
785                 790                 795                 800
Thr Ile Ser Leu Ser Leu Val Gly Ile Leu Leu Gly Ile Tyr Leu Gly
            805                 810                 815
Lys Gly Leu His Thr Tyr Ile Met Thr Met Ile Ser Thr Gly Asp Ile
            820                 825                 830
Gln Phe Gly Val Lys Val Asp Ala Tyr Val Tyr Leu Val Pro Ile Leu
            835                 840                 845
Val Ile Leu Ser Leu Leu Ala Val Leu Gly Ile Trp Val Asn Arg His
850                 855                 860
Leu Lys Lys Val Asp Met Leu Glu Ala Leu Lys Ser Ile Asp
865                 870                 875
```

<210> SEQ ID NO 43
<211> LENGTH: 1344
<212> TYPE: DNA
<213> ORGANISM: Streptococcus pyogenes

<400> SEQUENCE: 43

```
atgatgttaa cgaagggca  acttccctat agtgctgctt ttacaacagg agggctcttt      60
tactttgtta tcattgcatt aagttattat ttgggatcga cactttggct agtctttgtt    120
caggtgtttt gtttttactt atctggttta tatctttata aactcattaa ttatatgaca    180
ggctttcaaa aagtggcttt aacttttca  attagctact atttattatc tgttagtctt    240
ggttttgggg gattgtatcc tactcaactg gctatgccat ttatattaat atcggcttgg    300
```

```
ttttttaacta agtattttgc ctgtttagtg aaagatgagg catttattct ttttggcttt     360
gtaggtgctc ttgcaatgct aattgacccg agtacccta tcttttggtc ttttgcttgt      420
gtgacagttt tttcttataa tataagccaa aagcatcttg caagaggttt ttatcaactg     480
ctagcttcga ttttttggaat gatttagtt ttttacacag caggatatt catttgaac      540 ttacaagtgc taaatcctta tttatcacaa acgatgattt atccttttac ttttttttaaa    600 tcaggaaact tatcgttgct ttttggactg gctattcagt tgttcttcgc ttttgggctt     660
ggtcttttga cgggaatgga gaatgtcatt aggcgattta aaaacaattc tgatagggtc     720
gtcaagtggc tatttgtcat ggtcattcta gaatctatac ttgtggctat attttcacaa     780
gactatcgcc cctatcatct tttacctctt ttaccttttg gattaatttt gactgctatt     840
cctgttggct atcagtatgg tataggatta ggtcagagta gtcatcgcag acgtcatggt     900
aaaaatggtg ttggtcgagt aatgatgatt tatcttaaga gacactttta tttgccaatt     960
ttaattgtag ggacaatact aatctgttct acttattgtt tcattagtag tattcctctt    1020
aatcaggagc gtgatcatat tgctagttat ttagaacaga actaaataa aactcaatct    1080 atttatgttt gggatgatac ttctaaaatt tatttggaca gtaaagctaa atctgtttct    1140
caatttagtt ctcctgacat caatacgcaa aagagagtc atcgaaaaat attagaagat    1200
gaactattag aaaataaggc tgcttatatc gttgttaatc gctataaaaa cctgcctaaa    1260
atcattcaaa aagtattatc tactaattac aaagtagata aacagataac gacaaaaagt    1320
tttattgttt atcagaaaaa gtaa                                            1344
```

<210> SEQ ID NO 44
<211> LENGTH: 447
<212> TYPE: PRT
<213> ORGANISM: Streptococcus pyogenes

<400> SEQUENCE: 44

```
Met Met Leu Thr Lys Gly Gln Leu Pro Tyr Ser Ala Ala Phe Thr Thr
1               5                   10                  15

Gly Gly Leu Phe Tyr Phe Val Ile Ile Ala Leu Ser Tyr Tyr Leu Gly
            20                  25                  30

Ser Thr Leu Trp Leu Val Phe Gln Val Phe Cys Phe Tyr Leu Ser
        35                  40                  45

Gly Leu Tyr Leu Tyr Lys Leu Ile Asn Tyr Met Thr Gly Phe Gln Lys
    50                  55                  60

Val Ala Leu Thr Phe Ser Ile Ser Tyr Tyr Leu Ser Val Ser Leu
65                  70                  75                  80

Gly Phe Gly Gly Leu Tyr Pro Thr Gln Leu Ala Met Pro Phe Ile Leu
                85                  90                  95

Ile Ser Ala Trp Phe Leu Thr Lys Tyr Phe Ala Cys Leu Val Lys Asp
            100                 105                 110

Glu Ala Phe Ile Leu Phe Gly Phe Val Gly Ala Leu Ala Met Leu Ile
        115                 120                 125

Asp Pro Ser Thr Leu Ile Phe Trp Ser Phe Ala Cys Val Thr Val Phe
    130                 135                 140

Ser Tyr Asn Ile Ser Gln Lys His Leu Ala Arg Gly Phe Tyr Gln Leu
145                 150                 155                 160

Leu Ala Ser Ile Phe Gly Met Ile Leu Val Phe Tyr Thr Ala Gly Tyr
                165                 170                 175

Phe Ile Leu Asn Leu Gln Val Leu Asn Pro Tyr Leu Ser Gln Thr Met
            180                 185                 190
```

Ile Tyr Pro Phe Thr Phe Phe Lys Ser Gly Asn Leu Ser Leu Leu Phe
            195                 200                 205

Gly Leu Ala Ile Gln Leu Phe Phe Ala Leu Gly Leu Gly Leu Leu Thr
            210                 215                 220

Gly Met Glu Asn Val Ile Arg Arg Phe Lys Asn Asn Ser Asp Arg Val
225                 230                 235                 240

Val Lys Trp Leu Phe Val Met Val Ile Leu Glu Ser Ile Leu Val Ala
                245                 250                 255

Ile Phe Ser Gln Asp Tyr Arg Pro Tyr His Leu Leu Pro Leu Leu Pro
            260                 265                 270

Phe Gly Leu Ile Leu Thr Ala Ile Pro Val Gly Tyr Gln Tyr Gly Ile
            275                 280                 285

Gly Leu Gly Gln Ser Ser His Arg Arg His Gly Lys Asn Gly Val
            290                 295                 300

Gly Arg Val Met Met Ile Tyr Leu Lys Arg His Phe Tyr Leu Pro Ile
305                 310                 315                 320

Leu Ile Val Gly Thr Ile Leu Ile Cys Ser Thr Tyr Cys Phe Ile Ser
                325                 330                 335

Ser Ile Pro Leu Asn Gln Glu Arg Asp His Ile Ala Ser Tyr Leu Glu
            340                 345                 350

Gln Lys Leu Asn Lys Thr Gln Ser Ile Tyr Val Trp Asp Asp Thr Ser
            355                 360                 365

Lys Ile Tyr Leu Asp Ser Lys Ala Lys Ser Val Ser Gln Phe Ser Ser
            370                 375                 380

Pro Asp Ile Asn Thr Gln Lys Glu Ser His Arg Lys Ile Leu Glu Asp
385                 390                 395                 400

Glu Leu Leu Glu Asn Lys Ala Ala Tyr Ile Val Asn Arg Tyr Lys
                405                 410                 415

Asn Leu Pro Lys Ile Ile Gln Lys Val Leu Ser Thr Asn Tyr Lys Val
            420                 425                 430

Asp Lys Gln Ile Thr Thr Lys Ser Phe Ile Val Tyr Gln Lys Lys
            435                 440                 445

<210> SEQ ID NO 45
<211> LENGTH: 324
<212> TYPE: DNA
<213> ORGANISM: Streptococcus pyogenes

<400> SEQUENCE: 45
atgcagtttt tacaaaaatg gtttaaacac tctaaaaaag agaagttgaa agaatcctcg      60
tcccttagta cagaaataga accttctgaa aactgggcaa agattcccgc ttatattcct     120
gcagacaaaa gtgattacaa aaaggttact ttaattacca gtgttattgc tgctgggcga     180
tagacctaat agtcaattca aggttaaacg cattctcaag cgcaatcctg aggcaatcac     240
tgtttcttta attgcttcaa gtatcgctgc aggtgtttac ccagaaagtc agtttcgggt     300
gacatccatc tattgcaaaa gtaa                                            324

<210> SEQ ID NO 46
<211> LENGTH: 107
<212> TYPE: PRT
<213> ORGANISM: Streptococcus pyogenes

<400> SEQUENCE: 46

Met Gln Phe Leu Gln Lys Trp Phe Lys His Ser Lys Lys Glu Lys Leu
1               5                   10                  15

```
Lys Glu Ser Ser Pro Leu Ser Thr Glu Ile Glu Pro Ser Glu Asn Trp
            20                  25                  30

Glu Lys Ile Pro Ala Tyr Ile Pro Ala Asp Lys Ser Asp Tyr Lys Lys
        35                  40                  45

Val Thr Leu Ile Thr Ser Ala Ile Ala Ala Gly Asp Arg Pro Asn Ser
    50                  55                  60

Gln Phe Lys Val Lys Arg Ile Leu Lys Arg Asn Pro Glu Ala Ile Thr
65                  70                  75                  80

Val Ser Leu Ile Ala Ser Ser Ile Ala Ala Gly Val Tyr Pro Glu Ser
                85                  90                  95

Gln Phe Arg Val Thr Ser Ile Tyr Cys Lys Arg
                100                 105

<210> SEQ ID NO 47
<211> LENGTH: 288
<212> TYPE: DNA
<213> ORGANISM: Streptococcus pyogenes

<400> SEQUENCE: 47
atgacaaaac gtaattcaaa agcctatata ttatggcaaa aaattatcaa aattttagga     60
attattgcac taattggtac ttttttcctc gcttttggc tgtatagact aggtatatta    120
aacgatagta atgctcttaa agacttagtg cagcgctata gattatgggg gccgtttgtt    180
tttattgtcg tgcagatcat acagattgtt tttcctgtga ttcctggagg ccttacgaca    240
gttgcaggtt tttaatctt tggccctgt aacaggtttt atttataa                  288

<210> SEQ ID NO 48
<211> LENGTH: 95
<212> TYPE: PRT
<213> ORGANISM: Streptococcus pyogenes

<400> SEQUENCE: 48

Met Thr Lys Arg Asn Ser Lys Ala Tyr Ile Leu Trp Gln Lys Ile Ile
1               5                   10                  15

Lys Ile Leu Gly Ile Ile Ala Leu Ile Gly Thr Phe Phe Leu Ala Phe
            20                  25                  30

Trp Leu Tyr Arg Leu Gly Ile Leu Asn Asp Ser Asn Ala Leu Lys Asp
        35                  40                  45

Leu Val Gln Arg Tyr Arg Leu Trp Gly Pro Phe Val Phe Ile Val Val
    50                  55                  60

Gln Ile Ile Gln Ile Val Phe Pro Val Ile Pro Gly Gly Leu Thr Thr
65                  70                  75                  80

Val Ala Gly Phe Leu Ile Phe Gly Pro Cys Asn Arg Phe Tyr Leu
                85                  90                  95

<210> SEQ ID NO 49
<211> LENGTH: 1311
<212> TYPE: DNA
<213> ORGANISM: Streptococcus pyogenes

<400> SEQUENCE: 49
atgaataaat taaaaaaaga gattttatca gataactata accactttt tcattttttt     60 gcggttttta caggtatttt tgtcattatg actattatta tcttacagat tatgcggttt    120
ggcgtttatt cgtcagttga cagtagttta gtttctgtta gtaataatgc aagtagctat    180
gctaatcgta cgatggctag aatatcttct ttttactttg atactgaaaa taacattatt    240
```

-continued

```
aaggcgctgc ctgattcaga tagttctaag ttattaggaa cgcctgcagc taatacagat    300
atcattttgt ttagtgctaa tggaacaatt ttaaatgctt ttgatgcgtt ttctaactat    360
caaaattttc atttagataa acgccggttg gggagtattg aaaccaccag tttaatgaat    420
ttttatggac aagaagaaaa ataccatacg ataactgtag gggttcatat caaaaattat    480
cctgcagttg cctatatgat ggcagtagta aatgtggaac aattagaccg cgctaatgaa    540
cgttatgagc gcattattat tatagttatg agtgttttttt ggctaatttc tattttagca    600
agtatttatt tagccaagtg gagcagaaaa cctatttttag aaagctatga aaaacaaaaa    660
atgtttgttg aaaatgctag tcatgaatta aggaccccctt tggcggtctt acagaatcgt    720
ctggaatcgc tttttcgtaa gcccaacgaa acgatattag aaaatagtga gcatctcgct    780
tctagtttag acgaggttcg caacatgcgc atcttaacaa ctaatttatt aaatttagca    840
agacgagatg atggcattaa tccacagtgg actcatttag atacagattt ttttaatgct    900
atttttgaga attatgaact agttgctaaa gaatatggaa aaatattttta ttttcagaac    960 caagtcaata gatcgttaag aatggataag gctttactaa acaattaat aacgatttta    1020 tttgacaatg ctattaaata tacagataaa aatggtatta ttgaaattat agtgaaaaca    1080
acggacaaaa atttattaat ttctgttatt gataatggtc cagggataac agatgaagaa    1140
aagaaaaaga ttttttgatcg tttttatcga gttgacaaag ctagaacacg gcaaacaggt    1200
ggatttggct tggggttggc tttagctcag caaatcgtga tgtctttaaa aggaaatatt    1260
acagtaaagg ataatgatcc taaaggtagt attttttgaag tcaaactata a            1311
```

<210> SEQ ID NO 50
<211> LENGTH: 436
<212> TYPE: PRT
<213> ORGANISM: Streptococcus pyogenes

<400> SEQUENCE: 50

```
Met Asn Lys Leu Lys Lys Glu Ile Leu Ser Asp Asn Tyr Asn His Phe
1               5                   10                  15

Phe His Phe Phe Ala Val Phe Thr Gly Ile Phe Val Ile Met Thr Ile
            20                  25                  30

Ile Ile Leu Gln Ile Met Arg Phe Gly Val Tyr Ser Ser Val Asp Ser
        35                  40                  45

Ser Leu Val Ser Val Ser Asn Asn Ala Ser Ser Tyr Ala Asn Arg Thr
    50                  55                  60

Met Ala Arg Ile Ser Ser Phe Tyr Phe Asp Thr Glu Asn Asn Ile Ile
65                  70                  75                  80

Lys Ala Leu Pro Asp Ser Asp Ser Ser Lys Leu Leu Gly Thr Pro Ala
                85                  90                  95

Ala Asn Thr Asp Ile Ile Leu Phe Ser Ala Asn Gly Thr Ile Leu Asn
            100                 105                 110

Ala Phe Asp Ala Phe Ser Asn Tyr Gln Asn Phe His Leu Asp Lys Arg
        115                 120                 125

Arg Leu Gly Ser Ile Glu Thr Thr Ser Leu Met Asn Phe Tyr Gly Gln
    130                 135                 140

Glu Glu Lys Tyr His Thr Ile Thr Val Gly Val His Ile Lys Asn Tyr
145                 150                 155                 160

Pro Ala Val Ala Tyr Met Met Ala Val Val Asn Val Glu Gln Leu Asp
                165                 170                 175

Arg Ala Asn Glu Arg Tyr Glu Arg Ile Ile Ile Ile Val Met Ser Val
            180                 185                 190
```

Phe Trp Leu Ile Ser Ile Leu Ala Ser Ile Tyr Leu Ala Lys Trp Ser
            195                 200                 205

Arg Lys Pro Ile Leu Glu Ser Tyr Glu Lys Gln Lys Met Phe Val Glu
        210                 215                 220

Asn Ala Ser His Glu Leu Arg Thr Pro Leu Ala Val Leu Gln Asn Arg
225                 230                 235                 240

Leu Glu Ser Leu Phe Arg Lys Pro Asn Glu Thr Ile Leu Glu Asn Ser
                245                 250                 255

Glu His Leu Ala Ser Ser Leu Asp Glu Val Arg Asn Met Arg Ile Leu
            260                 265                 270

Thr Thr Asn Leu Leu Asn Leu Ala Arg Arg Asp Asp Gly Ile Asn Pro
        275                 280                 285

Gln Trp Thr His Leu Asp Thr Asp Phe Phe Asn Ala Ile Phe Glu Asn
290                 295                 300

Tyr Glu Leu Val Ala Lys Glu Tyr Gly Lys Ile Phe Tyr Phe Gln Asn
305                 310                 315                 320

Gln Val Asn Arg Ser Leu Arg Met Asp Lys Ala Leu Leu Lys Gln Leu
                325                 330                 335

Ile Thr Ile Leu Phe Asp Asn Ala Ile Lys Tyr Thr Asp Lys Asn Gly
            340                 345                 350

Ile Ile Glu Ile Ile Val Lys Thr Thr Asp Lys Asn Leu Leu Ile Ser
        355                 360                 365

Val Ile Asp Asn Gly Pro Gly Ile Thr Asp Glu Glu Lys Lys Lys Ile
370                 375                 380

Phe Asp Arg Phe Tyr Arg Val Asp Lys Ala Arg Thr Arg Gln Thr Gly
385                 390                 395                 400

Gly Phe Gly Leu Gly Leu Ala Leu Ala Gln Gln Ile Val Met Ser Leu
                405                 410                 415

Lys Gly Asn Ile Thr Val Lys Asp Asn Asp Pro Lys Gly Ser Ile Phe
            420                 425                 430

Glu Val Lys Leu
        435

<210> SEQ ID NO 51
<211> LENGTH: 699
<212> TYPE: DNA
<213> ORGANISM: Streptococcus pyogenes

<400> SEQUENCE: 51
atgttttctg acatcaact aaaaacagca cgattatcaa agggaataac tcaatcagaa      60
ttgggaagat tgttgcatgt caataaaatg acaatatcta attgggaaaa aggtaagaat     120
ataccaaatg aaaaacattt aaatgcctta ttgcatctat tcaatgtgac atctgattat     180
ttcgacccaa actatagatt gctaacgcct tataaccagc tgacaatatc taataaagaa     240
aaagtaattg ctattcaga gcgattgtta aatcatcaaa tagacaaaaa atctaaagat     300
ctcatagata aaccatcaca attatatgct tatcgggtct atgaaagttt atctgctggt     360
actggttact cctattttgg tgatggtaac tttgatgttg tcttttacga tgaacaatta     420
gaatacgatt ttgcgtcttg ggttttttgga gattctatgg agccaactta ttttaaatggt    480 gaagttgttc ttataaaaca aaatagtttt gattacgatg agcaattta tgcagtcgaa      540 tgggatgggc aaacatatat caaaaaggta tttcgtgaag atgagggatt acgtctagtg     600
tccttaaata aaaaatattc tgataagttt gctccctata gcgaagaacc tcgcattatt     660

-continued ggcaaaatta tcgctaattt taggcccta gaaatttaa    699

<210> SEQ ID NO 52
<211> LENGTH: 232
<212> TYPE: PRT
<213> ORGANISM: Streptococcus pyogenes

<400> SEQUENCE: 52

Met Phe Ser Gly His Gln Leu Lys Thr Ala Arg Leu Ser Lys Gly Ile
1               5                   10                  15

Thr Gln Ser Glu Leu Gly Arg Leu Leu His Val Asn Lys Met Thr Ile
            20                  25                  30

Ser Asn Trp Glu Lys Gly Lys Asn Ile Pro Asn Glu Lys His Leu Asn
        35                  40                  45

Ala Leu Leu His Leu Phe Asn Val Thr Ser Asp Tyr Phe Asp Pro Asn
    50                  55                  60

Tyr Arg Leu Leu Thr Pro Tyr Asn Gln Leu Thr Ile Ser Asn Lys Glu
65                  70                  75                  80

Lys Val Ile Gly Tyr Ser Glu Arg Leu Leu Asn His Gln Ile Asp Lys
                85                  90                  95

Lys Ser Lys Asp Leu Ile Asp Lys Pro Ser Gln Leu Tyr Ala Tyr Arg
            100                 105                 110

Val Tyr Glu Ser Leu Ser Ala Gly Thr Gly Tyr Ser Tyr Phe Gly Asp
        115                 120                 125

Gly Asn Phe Asp Val Val Phe Tyr Asp Glu Gln Leu Glu Tyr Asp Phe
    130                 135                 140

Ala Ser Trp Val Phe Gly Asp Ser Met Glu Pro Thr Tyr Leu Asn Gly
145                 150                 155                 160

Glu Val Val Leu Ile Lys Gln Asn Ser Phe Asp Tyr Asp Gly Ala Ile
                165                 170                 175

Tyr Ala Val Glu Trp Asp Gly Gln Thr Tyr Ile Lys Lys Val Phe Arg
            180                 185                 190

Glu Asp Glu Gly Leu Arg Leu Val Ser Leu Asn Lys Lys Tyr Ser Asp
        195                 200                 205

Lys Phe Ala Pro Tyr Ser Glu Glu Pro Arg Ile Ile Gly Lys Ile Ile
    210                 215                 220

Ala Asn Phe Arg Pro Leu Glu Ile
225                 230

<210> SEQ ID NO 53
<211> LENGTH: 1497
<212> TYPE: DNA
<213> ORGANISM: Streptococcus pyogenes

<400> SEQUENCE: 53
ttgaaaaggg ttcccgtaga aagagacaaa cgcttagtct ctttcttttt ctttcttctc    60
atttctgtta taataagtca ggtaactaca ttagaaagat tgtgggtct gtcatctaag    120 agatgtcatt cccgaagagg tattagtgac ttgtctcaat caactgcaac ttatattaat    180
gttattggag ctgggctagc tggttctgaa gctgcctatc agattgctaa gcgcggtatc    240
cccgttaaat tgtatgaaat gcgtggtgtc aaagcaacac cgcaacataa aaccactaat    300
tttgccgaat tggtctgttc caactcattt cgtggtgata gcttaaccaa tgcagtcggt    360
cttctcaaag aagaaatgcg gcgattagac tccattatta tgcgtaatgg tgaagctaac    420
cgcgtacctg ctgggggagc aatggctgtt gaccgtgagg ggtatgcaga gagtgtcact    480

-continued

```
gcagagttgg aaaatcatcc tctcattgag gtcattcgtg gtgaaattac agaaatccct    540
gacgatgcta tcacggttat cgcgacggga ccgctgactt cggatgccct ggcagaaaaa    600
attcacgcgc taaatggtgg cgacggattc tattttacg atgcagcagc gcctatcatt    660
gataaatcta ccattgatat gagcaaggtt taccttaaat ctcgctacga taaaggcgaa    720
gctgcttacc tcaactgccc tatgaccaaa gaagaattca tggctttcca tgaagctctg    780
acaaccgcag aagaagcccc gctgaatgcc tttgaaaaag aaaagtattt tgaaggctgt    840
atgccgattg aagttatggc taaacgtggc attaaaacca tgctttatgg acctatgaaa    900
cccgttggat tggaatatcc agatgactat acaggtcctc gcgatggaga atttaaaacg    960
ccatatgccg tcgtgcaatt gcgtcaagat aatgcagctg aagcctttta atatatcgtt   1020
ggtttccaaa cccatctcaa atggggtgag caaaaacgcg ttttccaaat gattccaggg   1080
cttgaaaatg ctgagtttgt ccgctacggc gtcatgcatc gcaattccta tatggattca   1140
ccaaatcttt taaccgaaac cttccaatct cggagcaatc caaaccttt ctttgcaggt   1200
cagatgactg gagttgaagg ttatgtcgaa tcagctgctt caggtttagt agcaggaatc   1260
aatgctgctc gtttgttcaa aagagaagaa gcacttattt ttcctcagac aacagctatt   1320
gggagtttgc ctcattatgt gactcatgcc gacagtaagc atttccaacc aatgaacgtc   1380
aactttggca tcatcaaaga gttagaaggc ccacgcattc gtgacaaaaa agaacgttat   1440
gaagctattg ctagtcgtgc tttggcagat ttagacacct gcttagcgtc gcttaa       1497
```

<210> SEQ ID NO 54
<211> LENGTH: 498
<212> TYPE: PRT
<213> ORGANISM: Streptococcus pyogenes

<400> SEQUENCE: 54

```
Leu Lys Arg Val Pro Val Glu Arg Asp Lys Arg Leu Val Ser Phe Phe
  1               5                  10                  15

Phe Phe Leu Leu Ile Ser Val Ile Ser Gln Val Thr Thr Leu Glu
             20                  25                  30

Arg Phe Val Gly Leu Ser Ser Lys Arg Cys His Ser Arg Arg Gly Ile
         35                  40                  45

Ser Asp Leu Ser Gln Ser Thr Ala Thr Tyr Ile Asn Val Ile Gly Ala
     50                  55                  60

Gly Leu Ala Gly Ser Glu Ala Ala Tyr Gln Asn Ala Lys Arg Gly Ile
 65                  70                  75                  80

Pro Val Lys Leu Tyr Glu Met Arg Gly Val Lys Ala Thr Pro Gln His
                 85                  90                  95

Lys Thr Thr Asn Phe Ala Glu Leu Val Cys Ser Asn Ser Phe Arg Gly
            100                 105                 110

Asp Ser Leu Thr Asn Ala Val Gly Leu Leu Lys Glu Glu Met Arg Arg
        115                 120                 125

Leu Asp Ser Ile Ile Met Arg Asn Gly Glu Ala Asn Arg Val Pro Ala
    130                 135                 140

Gly Gly Ala Met Ala Val Asp Arg Glu Gly Tyr Ala Glu Ser Val Thr
145                 150                 155                 160

Ala Glu Leu Glu Asn His Pro Leu Ile Glu Val Ile Arg Gly Glu Ile
                165                 170                 175

Thr Glu Ile Pro Asp Asp Ala Ile Thr Val Ile Ala Thr Gly Pro Leu
            180                 185                 190

Thr Ser Asp Ala Leu Ala Glu Lys Ile His Ala Leu Asn Gly Gly Asp
```

```
                195                 200                 205
Gly Phe Tyr Phe Tyr Asp Ala Ala Pro Ile Ile Asp Lys Ser Thr
210                 215                 220
Ile Asp Met Ser Lys Val Tyr Leu Lys Ser Arg Tyr Asp Lys Gly Glu
225                 230                 235                 240
Ala Ala Tyr Leu Asn Cys Pro Met Thr Lys Glu Phe Met Ala Phe
            245                 250                 255
His Glu Ala Leu Thr Thr Ala Glu Glu Ala Pro Leu Asn Ala Phe Glu
            260                 265                 270
Lys Glu Lys Tyr Phe Glu Gly Cys Met Pro Ile Glu Val Met Ala Lys
    275                 280                 285
Arg Gly Ile Lys Thr Met Leu Tyr Gly Pro Met Lys Pro Val Gly Leu
290                 295                 300
Glu Tyr Pro Asp Asp Tyr Thr Gly Pro Arg Asp Gly Glu Phe Lys Thr
305                 310                 315                 320
Pro Tyr Ala Val Val Gln Leu Arg Gln Asp Asn Ala Ala Gly Ser Leu
                325                 330                 335
Tyr Asn Ile Val Gly Phe Gln Thr His Leu Lys Trp Gly Glu Gln Lys
            340                 345                 350
Arg Val Phe Gln Met Ile Pro Gly Leu Glu Asn Ala Glu Phe Val Arg
    355                 360                 365
Tyr Gly Val Met His Arg Asn Ser Tyr Met Asp Ser Pro Asn Leu Leu
370                 375                 380
Thr Glu Thr Phe Gln Ser Arg Ser Asn Pro Asn Leu Phe Phe Ala Gly
385                 390                 395                 400
Gln Met Thr Gly Val Glu Gly Tyr Val Glu Ser Ala Ala Ser Gly Leu
                405                 410                 415
Val Ala Gly Ile Asn Ala Ala Arg Leu Phe Lys Arg Glu Glu Ala Leu
            420                 425                 430
Ile Phe Pro Gln Thr Thr Ala Ile Gly Ser Leu Pro His Tyr Val Thr
    435                 440                 445
His Ala Asp Ser Lys His Phe Gln Pro Met Asn Val Asn Phe Gly Ile
450                 455                 460
Ile Lys Glu Leu Glu Gly Pro Arg Ile Arg Asp Lys Lys Glu Arg Tyr
465                 470                 475                 480
Glu Ala Ile Ala Ser Arg Ala Leu Ala Asp Leu Asp Thr Cys Leu Ala
                485                 490                 495
Ser Leu
```

<210> SEQ ID NO 55
<211> LENGTH: 1539
<212> TYPE: DNA
<213> ORGANISM: Streptococcus pyogenes

<400> SEQUENCE: 55

```
atgattaagg atatgattga cagtattgag cagtttgctc agacacaggc tgattttcca      60
gtttatgatt gtttagggga acgccgcact tacggacaac tcaaaagaga ttctgatagc     120
attgctgcat ttatagatag cttagcttta ctggcaaaat ctccagtttt ggttttgggg     180
gcgcaaactt atgatatgtt agctactttt gtagctttaa ccaaatctgg tcatgcctat     240
atcccagtag atgtgcattc agcaccagaa cgtatttttag cgattattga gattgcaaag     300
cccagtttaa tcattgctat tgaggaattc cctcttacta ttgaagggat ttcccttgtc     360
tcactatcag agattgagtc agcaaaatta gcagaaatgc cctatgagcg aacacattct     420
```

-continued

```
gttaaaggag atgataatta ttacattatt ttcacctctg aacaacggg ccaaccaaaa      480 ggggtgcaaa tttcacatga caatcttttg agctttacca actggatgat cgaagatgca      540
gcatttgatg tacctaaaca gccacaaatg ctggcgcagc caccctattc ctttgacctt      600
tctgtcatgt actgggcacc taccttggct ttaggtggaa ccttatttgc acttccaaaa      660
gaattggtgg cagactttaa acagttattt acaacgattg cgcaacttcc agttggcatt      720
tggacatcga ctccttcatt tgctgatatg gccatgctta gcgatgattt ttgccaggct      780
aagatgccag ctttaacgca ttttattttt gatggcgaag aattaaccgt ttctacggct      840
cgaaaactct ttgaacgttt cccgagtgcc aagattatca atgcctatgg accaacagaa      900
gcgactgtag cctatccgc tattgaaatt accagagaaa tggtggataa ttatacccgc      960
ttgccgattg ctaccccaa accagattct ccgacctata ttattgatga agatggtaag     1020
gagttatctt caggggagca gggtgaaatt attgttacag gcctgctgt gtcaaaaggt     1080 tacctcaaca atcctgagaa aaccgcagaa gctttcttta cttttaaagg acagcctgct     1140
tatcatacag gggacattgg ctcactgaca gaagataata ttttgttgta tggtgggcgt     1200
ttggattttc agattaaata tgctggttat cgtattgaac tagaagatgt ttcccaacag     1260
ttgaatcaat caccaatggt agcatcggct gtggctgttc caaggtacaa taaagaacat     1320
aaggttcaaa atctcttggc ctatatcgtt gtcaaagatg gggttaaaga gcgttttgat     1380
agggaattgg agttaaccaa agctatcaaa gcctctgtta aggatcatat gatgagttat     1440
atgatgcctt ctaagtttct ttatcgagat agtctaccat taactccaaa tggtaagata     1500
gatattaaaa ctttgattaa tgaggtcaat aaccgataa                             1539
```

<210> SEQ ID NO 56
<211> LENGTH: 512
<212> TYPE: PRT
<213> ORGANISM: Streptococcus pyogenes

<400> SEQUENCE: 56

```
Met Ile Lys Asp Met Ile Asp Ser Ile Glu Gln Phe Ala Gln Thr Gln
1               5                  10                  15

Ala Asp Phe Pro Val Tyr Asp Cys Leu Gly Glu Arg Arg Thr Tyr Gly
                20                  25                  30

Gln Leu Lys Arg Asp Ser Asp Ser Ile Ala Ala Phe Ile Asp Ser Leu
            35                  40                  45

Ala Leu Leu Ala Lys Ser Pro Val Leu Val Phe Gly Ala Gln Thr Tyr
        50                  55                  60

Asp Met Leu Ala Thr Phe Val Ala Leu Thr Lys Ser Gly His Ala Tyr
65                  70                  75                  80

Ile Pro Val Asp Val His Ser Ala Pro Glu Arg Ile Leu Ala Ile Ile
                85                  90                  95

Glu Ile Ala Lys Pro Ser Leu Ile Ile Ala Ile Glu Glu Phe Pro Leu
                100                 105                 110

Thr Ile Glu Gly Ile Ser Leu Val Ser Leu Ser Glu Ile Glu Ser Ala
            115                 120                 125

Lys Leu Ala Glu Met Pro Tyr Glu Arg Thr His Ser Val Lys Gly Asp
        130                 135                 140

Asp Asn Tyr Tyr Ile Ile Phe Thr Ser Gly Thr Thr Gly Gln Pro Lys
145                 150                 155                 160

Gly Val Gln Ile Ser His Asp Asn Leu Leu Ser Phe Thr Asn Trp Met
                165                 170                 175
```

```
Ile Glu Asp Ala Ala Phe Asp Val Pro Lys Gln Pro Gln Met Leu Ala
            180                 185                 190

Gln Pro Pro Tyr Ser Phe Asp Leu Ser Val Met Tyr Trp Ala Pro Thr
        195                 200                 205

Leu Ala Leu Gly Gly Thr Leu Phe Ala Leu Pro Lys Glu Leu Val Ala
    210                 215                 220

Asp Phe Lys Gln Leu Phe Thr Thr Ile Ala Gln Leu Pro Val Gly Ile
225                 230                 235                 240

Trp Thr Ser Thr Pro Ser Phe Ala Asp Met Ala Met Leu Ser Asp Asp
                245                 250                 255

Phe Cys Gln Ala Lys Met Pro Ala Leu Thr His Phe Tyr Phe Asp Gly
            260                 265                 270

Glu Glu Leu Thr Val Ser Thr Ala Arg Lys Leu Phe Glu Arg Phe Pro
        275                 280                 285

Ser Ala Lys Ile Ile Asn Ala Tyr Gly Pro Thr Glu Ala Thr Val Ala
    290                 295                 300

Leu Ser Ala Ile Glu Ile Thr Arg Glu Met Val Asp Asn Tyr Thr Arg
305                 310                 315                 320

Leu Pro Ile Gly Tyr Pro Lys Pro Asp Ser Pro Thr Tyr Ile Ile Asp
                325                 330                 335

Glu Asp Gly Lys Glu Leu Ser Ser Gly Glu Gln Gly Glu Ile Ile Val
            340                 345                 350

Thr Gly Pro Ala Val Ser Lys Gly Tyr Leu Asn Asn Pro Glu Lys Thr
        355                 360                 365

Ala Glu Ala Phe Phe Thr Phe Lys Gly Gln Pro Ala Tyr His Thr Gly
    370                 375                 380

Asp Ile Gly Ser Leu Thr Glu Asp Asn Ile Leu Leu Tyr Gly Gly Arg
385                 390                 395                 400

Leu Asp Phe Gln Ile Lys Tyr Ala Gly Tyr Arg Ile Glu Leu Glu Asp
                405                 410                 415

Val Ser Gln Gln Leu Asn Gln Ser Pro Met Val Ala Ser Ala Val Ala
            420                 425                 430

Val Pro Arg Tyr Asn Lys Glu His Lys Val Gln Asn Leu Leu Ala Tyr
        435                 440                 445

Ile Val Val Lys Asp Gly Val Lys Glu Arg Phe Asp Arg Glu Leu Glu
    450                 455                 460

Leu Thr Lys Ala Ile Lys Ala Ser Val Lys Asp His Met Met Ser Tyr
465                 470                 475                 480

Met Met Pro Ser Lys Phe Leu Tyr Arg Asp Ser Leu Pro Leu Thr Pro
                485                 490                 495

Asn Gly Lys Ile Asp Ile Lys Thr Leu Ile Asn Glu Val Asn Asn Arg
            500                 505                 510

<210> SEQ ID NO 57
<211> LENGTH: 1278
<212> TYPE: DNA
<213> ORGANISM: Streptococcus pyogenes

<400> SEQUENCE: 57
atgacaaaaa ctaatcttaa ctggagcggt ttttcaaaga aacattcga agaacgcctc      60 caacttatcg aaaaatttaa actacttaat gctgaaaact taaatcaact caaaacagac     120
gttcttttgc ctatccaaac agctaatcaa atgactgaaa atgtcttagg acgattggct     180
ttgcccttta gcatagctcc tgattttctt gtcaacggtt caacttatca gatgcctttt     240
```

-continued

```
gtcacggaag aaccttctgt tgttgctgca gcatctttcg cagcaaaact aatcaaacgc      300
tcaggtggtt ttaaagctca aaccctaaac cgacaaatga ttggtcaaat tgttctttac      360
gatatcgacc aaatagataa cgctaaagcc gccatccttc ataaaacaaa aaagctaatt      420
gcattggcaa ataaagctta tccttccatt gttaaaagag gtggaggcgc tagaaccatt      480
catttggaag aaaaaggaga attttttgatt ttctatctga ctgttgatac ccaagaagct      540
atgggagcaa atatggtcaa tactatgatg gaagctcttg ttcctgattt aacaagactg      600
tctaaggggc attgtctaat ggcgatttta tctaattacg caacagagtc gcttgttact      660
actagttgtg agattcccgt gcgccttttta gatcacgata aaacaaaatc cctacagtta      720
gctcaaaaaa tagagctagc cagccgacta gctcaagtag atccttaccg ggctactact      780
cataataaag gtattttttaa tggcattgat gcagtggtaa tagccacagg aaatgactgg      840
cgtgctattg aagcaggggc ccatgcttat gcctcaagaa atggtagcta tcaaggactt      900
agtcagtggc attttgacca agataaacaa gttctgcttg gccaaatgac cctccctatg      960
cctattgcta gtaagggggg atctatcggg cttaaccta ctgtttctat cgcacatgat     1020
cttcttaatc aacctgatgc caaaacatta gcccaattga ttgcatctgt ggggttagct     1080
caaaactttg ctgcactaaa agctctgacc tcatctggca tccaagctgg tcacatgaaa     1140
ctacatgcga aatcattagc tcttttggcg ggggcaaccc aagacgaaat tgctccttta     1200
gttaatgctt tactagctga taaaccaata aatctagaaa aagcacattt ttacttatcc     1260
cagctaagac agtcttaa                                                   1278
```

<210> SEQ ID NO 58
<211> LENGTH: 425
<212> TYPE: PRT
<213> ORGANISM: Streptococcus pyogenes

<400> SEQUENCE: 58

```
Met Thr Lys Thr Asn Leu Asn Trp Ser Gly Phe Ser Lys Lys Thr Phe
1               5                   10                  15

Glu Glu Arg Leu Gln Leu Ile Glu Lys Phe Lys Leu Leu Asn Ala Glu
            20                  25                  30

Asn Leu Asn Gln Leu Lys Thr Asp Val Leu Leu Pro Ile Gln Thr Ala
        35                  40                  45

Asn Gln Met Thr Glu Asn Val Leu Gly Arg Leu Ala Leu Pro Phe Ser
    50                  55                  60

Ile Ala Pro Asp Phe Leu Val Asn Gly Ser Thr Tyr Gln Met Pro Phe
65                  70                  75                  80

Val Thr Glu Glu Pro Ser Val Val Ala Ala Ser Phe Ala Ala Lys
                85                  90                  95

Leu Ile Lys Arg Ser Gly Gly Phe Lys Ala Gln Thr Leu Asn Arg Gln
            100                 105                 110

Met Ile Gly Gln Ile Val Leu Tyr Asp Ile Asp Gln Ile Asp Asn Ala
        115                 120                 125

Lys Ala Ala Ile Leu His Lys Thr Lys Lys Leu Ile Ala Leu Ala Asn
    130                 135                 140

Lys Ala Tyr Pro Ser Ile Val Lys Arg Gly Gly Ala Arg Thr Ile
145                 150                 155                 160

His Leu Glu Glu Lys Gly Glu Phe Leu Ile Phe Tyr Leu Thr Val Asp
                165                 170                 175

Thr Gln Glu Ala Met Gly Ala Asn Met Val Asn Thr Met Met Glu Ala
```

```
                180             185             190
Leu Val Pro Asp Leu Thr Arg Leu Ser Lys Gly His Cys Leu Met Ala
        195                 200                 205
Ile Leu Ser Asn Tyr Ala Thr Glu Ser Leu Val Thr Thr Ser Cys Glu
    210                 215                 220
Ile Pro Val Arg Leu Leu Asp His Asp Lys Thr Lys Ser Leu Gln Leu
225                 230                 235                 240
Ala Gln Lys Ile Glu Leu Ala Ser Arg Leu Ala Gln Val Asp Pro Tyr
                245                 250                 255
Arg Ala Thr Thr His Asn Lys Gly Ile Phe Asn Gly Ile Asp Ala Val
            260                 265                 270
Val Ile Ala Thr Gly Asn Asp Trp Arg Ala Ile Glu Ala Gly Ala His
        275                 280                 285
Ala Tyr Ala Ser Arg Asn Gly Ser Tyr Gln Gly Leu Ser Gln Trp His
    290                 295                 300
Phe Asp Gln Asp Lys Gln Val Leu Leu Gly Gln Met Thr Leu Pro Met
305                 310                 315                 320
Pro Ile Ala Ser Lys Gly Gly Ser Ile Gly Leu Asn Pro Thr Val Ser
                325                 330                 335
Ile Ala His Asp Leu Leu Asn Gln Pro Asp Ala Lys Thr Leu Ala Gln
            340                 345                 350
Leu Ile Ala Ser Val Gly Leu Ala Gln Asn Phe Ala Ala Leu Lys Ala
        355                 360                 365
Leu Thr Ser Ser Gly Ile Gln Ala Gly His Met Lys Leu His Ala Lys
    370                 375                 380
Ser Leu Ala Leu Leu Ala Gly Ala Thr Gln Asp Glu Ile Ala Pro Leu
385                 390                 395                 400
Val Asn Ala Leu Leu Ala Asp Lys Pro Ile Asn Leu Glu Lys Ala His
                405                 410                 415
Phe Tyr Leu Ser Gln Leu Arg Gln Ser
            420                 425

<210> SEQ ID NO 59
<211> LENGTH: 915
<212> TYPE: DNA
<213> ORGANISM: Streptococcus pyogenes

<400> SEQUENCE: 59
atggtattat ttacaggaaa acagtcgaa  gaagctatcg aaacaggact tcaagagtta    60
gggttatcac gccttaaagc gcatatcaaa gtcatttcaa aagagaaaaa aggtttcctc   120
gggtttggta aaagccagc  ccaagttgat atcgaaggta tcagcgacaa gacggtttat   180
aaggctgata aaaagccac  tcgaggtgtt ccagaggata ttaatcgtca aaatactccc   240
gcggtcaatt ctgctgatgt agaacctgaa gaaataaaag ccactcaaag gttagaagca   300
gaagatacca agtggttcc  tctcatgtct gaagatagtc agcgcaaac  ccttctaat   360 cttgctgaga cagtcactga acaaaaagca caacaaccgt caatcccagt cgaagaatca   420
gaagtgcccc aagatgctgg taatgatggt ttcagcaaag atattgaaaa agctgctcag   480
gaagtgtccg attatgtgac taaaattatc tatgaaatgg atatcgaagc taccgttgaa   540
accagcaaca atcgtcgcca aatcaatttg cagattgaaa cgccagaggc gggacgtgtg   600
attggttacc atggtaaggt cttgaaatcc ttgcagttgt tagctcaaaa tttcttgcac   660
gaccgctatt caaaaaattt ttcagtatcc ttgaatgtcc atgattatgt ggaacatcga   720
```

```
acagaaacct tgattgactt tacgcaaaaa gttgccaaac gcgttttgga atctggtcaa    780
gattacacca tggatcccat gagtaacagt gagcgtaaaa tcgttcataa aaccgtttca    840
tccattgaag gggttgatag ttattctgaa ggcaatgacc ctaaccgcta tgtggtagtc    900
agtcttcaac gttaa                                                    915
```

<210> SEQ ID NO 60
<211> LENGTH: 304
<212> TYPE: PRT
<213> ORGANISM: Streptococcus pyogenes

<400> SEQUENCE: 60

```
Met Val Leu Phe Thr Gly Lys Thr Val Glu Glu Ala Ile Glu Thr Gly
1               5                   10                  15

Leu Gln Glu Leu Gly Leu Ser Arg Leu Lys Ala His Ile Lys Val Ile
            20                  25                  30

Ser Lys Glu Lys Lys Gly Phe Leu Gly Phe Gly Lys Lys Pro Ala Gln
        35                  40                  45

Val Asp Ile Glu Gly Ile Ser Asp Lys Thr Val Tyr Lys Ala Asp Lys
    50                  55                  60

Lys Ala Thr Arg Gly Val Pro Glu Asp Ile Asn Arg Gln Asn Thr Pro
65                  70                  75                  80

Ala Val Asn Ser Ala Asp Val Glu Pro Glu Ile Lys Ala Thr Gln
            85                  90                  95

Arg Leu Glu Ala Glu Asp Thr Lys Val Val Pro Leu Met Ser Glu Asp
            100                 105                 110

Ser Pro Ala Gln Thr Pro Ser Asn Leu Ala Glu Thr Val Thr Glu Thr
        115                 120                 125

Lys Ala Gln Gln Pro Ser Ile Pro Val Glu Glu Ser Glu Val Pro Gln
    130                 135                 140

Asp Ala Gly Asn Asp Gly Phe Ser Lys Asp Ile Glu Lys Ala Ala Gln
145                 150                 155                 160

Glu Val Ser Asp Tyr Val Thr Lys Ile Ile Tyr Glu Met Asp Ile Glu
            165                 170                 175

Ala Thr Val Glu Thr Ser Asn Asn Arg Arg Gln Ile Asn Leu Gln Ile
            180                 185                 190

Glu Thr Pro Glu Ala Gly Arg Val Ile Gly Tyr His Gly Lys Val Leu
        195                 200                 205

Lys Ser Leu Gln Leu Leu Ala Gln Asn Phe Leu His Asp Arg Tyr Ser
    210                 215                 220

Lys Asn Phe Ser Val Ser Leu Asn Val His Asp Tyr Val Glu His Arg
225                 230                 235                 240

Thr Glu Thr Leu Ile Asp Phe Thr Gln Lys Val Ala Lys Arg Val Leu
            245                 250                 255

Glu Ser Gly Gln Asp Tyr Thr Met Asp Pro Met Ser Asn Ser Glu Arg
            260                 265                 270

Lys Ile Val His Lys Thr Val Ser Ser Ile Glu Gly Val Asp Ser Tyr
        275                 280                 285

Ser Glu Gly Asn Asp Pro Asn Arg Tyr Val Val Ser Leu Gln Arg
    290                 295                 300
```

<210> SEQ ID NO 61
<211> LENGTH: 1269
<212> TYPE: DNA
<213> ORGANISM: Streptococcus pyogenes

```
<400> SEQUENCE: 61
atgacaacaa aatatcaaac aatcatttcc aatatcgaac aagatatcca gaaacagcga       60
ctaaaaaaag gggacaagct accttcaatt agggtactaa gtaaggttta ttattgtagc      120
aaagatactg ttcagcgggc tcttttagaa ttaaaatatc gtcacttaat ttatgctgtt      180
cctaaaagtg gttattatgt tttgggtaac gtaagcatgc ccgataatgt tcttaatcta      240
agtcttgaag attataataa tatggcttat gaagatttcc gactctgctt aaatgaggcc      300
ttaagtgcta agacaaaata cctctttcat tattatcaca aaaccgaagg actagaagaa      360
ctaagggaag ctttgcttct ttacttagct gaaaatagtg tttacagtaa caagaccaa       420
ctattaatca cctctgggac gcaacaagcg ctttatattt tatcacaaat gccttttcct      480
aatacgggca aaacaattct ccttgaaaag cctacttatc atcggatgga agctattgtt      540
gctcagttag gattacccta tcaaactatc tctagacact taatggcct tgatttagaa       600
ctcttagaat ctttatttca aactggcgat attaaatttt tttacacgat tcacgatttt     660
tcacatcctc tgggactttc ttatagcact aaggaaaagg aagctattgt tcgtctagca      720
caacgatacc aggtttatat tttagaagat gattatttag gagattttgt gaaacttaaa     780
gagccaccaa ttcattatta tgacactcat caccgaatca tctacctaaa atcttttca      840
atgagtgttt ttcctgcact ccgtatcgga gctctagttt taccgtcagg tttaaaacct      900
catttttaa cccaaaaatc attgattgat ttagacacga acttactaat gcaaaaagca      960
ttagctcttt atttagaaaa tgggatgttt caaaaaaatc ttcgctttat taagcgttat     1020
ctaaaacagc gggaacgtca attggctctc tttttaaaac aaaattgccc tgatattcac     1080
tatcaactaa ccccctactca tttagtgatt gattacacga catcagactc ttatagaaac   1140
tttacattag ataaatctga tagaataata ataactggaa aaaacgcta tctctctatt      1200
actatcaatc aacaaataca aagcaaatta aactcactaa tcaaaaatac ttgtggaaag    1260
agcaactaa                                                              1269

<210> SEQ ID NO 62
<211> LENGTH: 422
<212> TYPE: PRT
<213> ORGANISM: Streptococcus pyogenes

<400> SEQUENCE: 62

Met Thr Thr Lys Tyr Gln Thr Ile Ile Ser Asn Ile Glu Gln Asp Ile
1               5                   10                  15

Gln Lys Gln Arg Leu Lys Lys Gly Asp Lys Leu Pro Ser Ile Arg Val
            20                  25                  30

Leu Ser Lys Val Tyr Tyr Cys Ser Lys Asp Thr Val Gln Arg Ala Leu
        35                  40                  45

Leu Glu Leu Lys Tyr Arg His Leu Ile Tyr Ala Val Pro Lys Ser Gly
    50                  55                  60

Tyr Tyr Val Leu Gly Asn Val Ser Met Pro Asp Asn Val Leu Asn Leu
65                  70                  75                  80

Ser Leu Glu Asp Tyr Asn Asn Met Ala Tyr Glu Asp Phe Arg Leu Cys
                85                  90                  95

Leu Asn Glu Ala Leu Ser Ala Lys Asp Lys Tyr Leu Phe His Tyr Tyr
            100                 105                 110

His Lys Thr Glu Gly Leu Glu Glu Leu Arg Glu Ala Leu Leu Leu Tyr
        115                 120                 125

Leu Ala Glu Asn Ser Val Tyr Ser Asn Lys Asp Gln Leu Leu Ile Thr
```

-continued

```
              130                 135                 140
Ser Gly Thr Gln Gln Ala Leu Tyr Ile Leu Ser Gln Met Pro Phe Pro
145                 150                 155                 160

Asn Thr Gly Lys Thr Ile Leu Leu Glu Lys Pro Thr Tyr His Arg Met
                165                 170                 175

Glu Ala Ile Val Ala Gln Leu Gly Leu Pro Tyr Gln Thr Ile Ser Arg
                180                 185                 190

His Phe Asn Gly Leu Asp Leu Glu Leu Leu Glu Ser Leu Phe Gln Thr
            195                 200                 205

Gly Asp Ile Lys Phe Phe Tyr Thr Ile Ser Arg Phe Ser His Pro Leu
            210                 215                 220

Gly Leu Ser Tyr Ser Thr Lys Glu Lys Glu Ala Ile Val Arg Leu Ala
225                 230                 235                 240

Gln Arg Tyr Gln Val Tyr Ile Leu Glu Asp Asp Tyr Leu Gly Asp Phe
                245                 250                 255

Val Lys Leu Lys Glu Pro Pro Ile His Tyr Tyr Asp Thr His His Arg
                260                 265                 270

Ile Ile Tyr Leu Lys Ser Phe Ser Met Ser Val Phe Pro Ala Leu Arg
                275                 280                 285

Ile Gly Ala Leu Val Leu Pro Ser Gly Leu Lys Pro His Phe Leu Thr
            290                 295                 300

Gln Lys Ser Leu Ile Asp Leu Asp Thr Asn Leu Leu Met Gln Lys Ala
305                 310                 315                 320

Leu Ala Leu Tyr Leu Glu Asn Gly Met Phe Gln Lys Asn Leu Arg Phe
                325                 330                 335

Ile Lys Arg Tyr Leu Lys Gln Arg Glu Arg Gln Leu Ala Leu Phe Leu
                340                 345                 350

Lys Gln Asn Cys Pro Asp Ile His Tyr Gln Leu Thr Pro Thr His Leu
            355                 360                 365

Val Ile Asp Tyr Thr Thr Ser Asp Ser Tyr Arg Asn Phe Thr Leu Asp
            370                 375                 380

Lys Ser Asp Arg Ile Ile Ile Thr Gly Lys Lys Arg Tyr Leu Ser Ile
385                 390                 395                 400

Thr Ile Asn Gln Gln Ile Gln Ser Lys Leu Asn Ser Leu Ile Lys Asn
                405                 410                 415

Thr Cys Gly Lys Ser Asn
                420
```

VIRULENCE GENES, PROTEINS, AND THEIR USE

This application is a National Stage Application of International Application Number PCT/GB00/04997, filed Dec. 22, 2000, published, pursuant to PCT Article 21(2).

FIELD OF THE INVENTION

This invention relates to virulence genes and proteins, and their use. More particularly, it relates to genes and proteins/peptides obtained from *Streptococcus pyogenes*, and their use in therapy and in screening for drugs.

BACKGROUND OF THE INVENTION

Group A *Streptococcus* (GAS) is responsible for the majority of Streptococcal illnesses. An organism of particular interest is *S. pyogenes*, which is implicated in a wide range of non-invasive and invasive infections, such as impetigo, pharyngitis, necrotizing fasciitis, bacteraemia, streptococcal toxic shock syndrome (STSS), pneumonia and rheumatic fever.

Some GAS infections can be treated with antibiotics, including penicillin and erythromycin. However, due to the problems associated with resistance to antibiotics, and antibiotic-allergic patients, there is a need for further therapeutics which may be useful in treating of preventing GAS infection.

SUMMARY OF THE INVENTION

The present invention is based on the discovery of virulence genes in *S. pyogenes*.

According to a first aspect of the invention, a peptide of the invention is encoded by an operon including any of the nucleotide sequences identified herein as SEQ ID NOS. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 and 61 of *S. pyogenes* or a homologue thereof in a Gram-positive bacterium, or a functional fragment thereof, for therapeutic or diagnostic use.

The peptides may have many therapeutic uses for treating Group A Streptococcal infections, including use in vaccines for prophylactic application.

According to a second aspect, a polynucleotide encoding a peptide defined above, may also be useful for therapy or diagnosis.

According to a third aspect, the genes that encode the peptides may be utilised to prepare attenuated microorganisms. The attenuated microorganisms will usually have a mutation that disrupts the expression of one or more of the genes identified herein, to provide a strain that lacks virulence. These microorganisms will also have use in therapy and diagnosis.

According to a fourth aspect, the peptides, genes and attenuated microorganisms according to the invention may be used in the treatment or prevention of a condition associated with infection by Streptococcal or Gram-positive bacteria.

DESCRIPTION OF THE INVENTION

The present invention is based on the discovery of genes encoding peptides which are implicated in virulence. The peptides and genes of the invention are therefore useful for the preparation of therapeutic agents to treat infection. It should be understood that references to therapy also include preventative treatments, e.g. vaccination. Furthermore, while the products of the invention are intended primarily for treatment of infections in human patients, veterinary applications are also considered to be within the scope of the invention.

The present invention is described with reference to *Streptococcus pyogenes*. However, all the Group A streptococcal strains, and many other Gram-positive bacterial strains are likely to include related peptides or proteins having amino acid sequence identity or similarity to those identified herein. Organisms likely to contain the peptides include, but are not limited to the genera *Lactococcus, Enterococcus, Streptococcus* and *Staphylococcus*.

Preferably, the peptides that may be useful in the various aspects of the invention have greater than a 40% similarity with the peptides identified herein. More preferably, the peptides have greater than 60% sequence similarity. Most preferably, the peptides have greater than 80% sequence similarity, e.g. 95% similarity. With regard to the polynucleotide sequences identified herein, related polynucleotides that may be useful in the various aspects of the invention may have greater than 40% identity with the sequences identified herein. More preferably, the polynucleotide sequences have greater than 60% sequence identity. Most preferably, the polynucleotide sequences have greater than 80% sequence identity, e.g. 95% identity.

The terms "similarity" and "identity" are known in the art. The use of the term "identity" refers to a sequence comparison based on identical matches between correspondingly identical positions in the sequences being compared. The term "similarity" refers to a comparison between amino acid sequences, and takes into account not only identical amino acids in corresponding positions, but also functionally similar amino acids in corresponding positions. Thus similarity between polypeptide sequences indicates functional similarity, in addition to sequence similarity.

Levels of identity between gene sequences and levels of identity or similarity between amino acid sequences can be calculated using known methods. In relation to the present invention, publicly available computer based methods for determining identity and similarity include the BLASTP, BLASTN and FASTA (Atschul et al., J. Molec. Biol., 1990; 215:403–410), the BLASTX program available from NCBI, and the Gap program from Genetics Computer Group, Madison Wis. The levels of similarity and identity provided herein, were obtained using the Gap program, with a Gap penalty of 12 and a Gap length penalty of 4 for determining the amino acid sequence comparisons, and a Gap penalty of 50 and a Gap length penalty of 3 for the polynucleotide sequence comparisons.

Having characterised a gene according to the invention, it is possible to use the gene sequence to search for related genes or peptides in other microorganisms. This may be carried out by searching in existing databases, e.g. EMBL or GenBank.

Peptides or proteins according to the invention may be purified and isolated by methods known in the art. In particular, having identified the gene sequence, it will be possible to use recombinant techniques to express the genes in a suitable host. Active fragments and related molecules can be identified and may be useful in therapy. For example, the peptides or their active fragments may be used as antigenic determinants in a vaccine, to elicit an immune response. They may also be used in the preparation of antibodies, for passive immunisation, or diagnostic applications. Suitable antibodies include monoclonal antibodies, or fragments thereof, including single chain Fv fragments. Methods for the preparation of antibodies will be apparent to those skilled in the art.

Active fragments of the peptides are those that retain the biological function of the peptide. For example, when used to elicit an immune response, the fragment will be of sufficient size, such that antibodies generated from the fragment will discriminate between that peptide and other peptides on the bacterial microorganism. Typically, the fragment will be at least 30 nucleotides (10 amino acids) in size, preferably 60 nucleotides (20 amino acids) and most preferably greater than 90 nucleotides (30 amino acids) in size.

It should also be understood, that in addition to related molecules from other microorganisms, the invention encompasses modifications made to the peptides and polynucleotides identified herein which do not significantly alter the biological function. It will be apparent to the skilled person that the degeneracy of the genetic code can result in polynucleotides with minor base changes from those specified herein, but which nevertheless encode the same peptides. Complementary polynucleotides are also within the invention. Conservative replacements at the amino acid level are also envisaged, i.e. different acidic or basic amino acids may be substituted without substantial loss of function.

The preparation of vaccines based on attenuated microorganisms is known to those skilled in the art. Vaccine compositions can be formulated with suitable carriers or adjuvants, e.g. alum, as necessary or desired, to provide effective immunisation against infection. The preparation of vaccine formulations will be apparent to the skilled person. The attenuated microorganisms may be prepared with a mutation that disrupts the expression of any of the genes identified herein. The skilled person will be aware of methods for disrupting expression of particular genes. Techniques that may be used include insertional inactivation or gene deletion techniques. Attenuated microorganisms according to the invention may also comprise additional mutations in other genes, for example in a second gene identified herein or in a separate gene required for growth of the microorganism, e.g. an aro mutation. Attenuated microorganisms may also be used as carrier systems for the delivery of heterologous antigens, therapeutic proteins or nucleic acids (DNA or RNA). In this embodiment, the attenuated microorganisms are used to deliver a heterologous antigen, protein or nucleic acid to a particular site in vivo. Introduction of a heterologous antigen, peptide or nucleic acid into an attenuated microorganism can be carried out by conventional techniques, including the use of recombinant constructs, e.g. vectors, which comprise polynucleotides that express the heterologous antigen or therapeutic protein, and also include suitable promoter sequences. Alternatively, the gene that encodes the heterologous antigen or protein may be incorporated into the genome of the organism and the endogenous promoters used to control expression.

More generally, and as is well known to those skilled in the art, a suitable amount of an active component of the invention can be selected, for therapeutic use, as can suitable carriers or excipients, and routes of administration. These factors would be chosen or determined according to known criteria such as the nature/severity of the condition to be treated, the type and/or health of the subject etc.

In a separate embodiment, the products of the invention may be used in screening assays for the identification of potential antimicrobial drugs or for the detection for virulence. Routine screening assays are known to those skilled in the art, and can be adapted using the products of the invention in the appropriate way. For example, the products of the invention may be used as the target for a potential drug, with the ability of the drug to inactivate or bind to the target indicating its potential antimicrobial activity.

The various products of the invention may also be used in veterinary applications.

The following is a brief overview of the experimental procedure used to identify the virulence genes. The virulence genes in *S. pyogenes* were identified by using signature-tagged mutagenesis (STM) to screen an *S. pyogenes* mutant bank for attenuated mutants (Hensel et al., 1995. Science 269(5222):400–3).

Mutants were generated via Tn917 transposon insertion, using a plasmid vector. In addition to a fragment of Tn917, the vector comprised a spectromycin-resistance gene, a chloramphenicol-resistance gene (CAT gene) with a synthetic promoter, a Gram-negative origin of replication (rop.ori) and a cloning site for the STM tags. After ligating the tags into the vector, *E. coli* transformation was carried out, and 96 plasmids that hybridised with the original tags were selected.

The *S. pyogenes* strain B514-SM (type M50) was transformed with each of the 96 tagged plasmids, and transformants were selected by resistance to spectinomycin and chloramphenicol. For each of the transformed *S. pyogenes* strains, 20 mutants were generated via Tn917 transposon insertion to create a mutant bank.

The mutant bank was screened in either a skin invasive lesion model of mouse infection (Schrager et al., J. Clinical Investigation 1996; 98:1954–1958) or from a throat colonisation model of mouse infection (Husmann et al., Infection and Immunity, 1997; 65 (4):935–944).

In the skin model, five CD1 mice were each inoculated intradermally with $1\times10^8$ cells in a volume of 50 $\mu$l representing the collection of 96 distinct and readily distinguishable mutants. 48 hours after inoculation, samples were taken and bacteria recovered. The skin lesions were macerated in 2×BHI medium and bacteria liberated from the lesion by treatment in a stomacher for 10 minutes. The released bacteria were plated out and a minimum of 10,000 colonies recovered from a minimum of 3 mice. DNA was isolated from these samples and used to amplify the tagged DNA present in the recovered bacteria. The DNA isolated from each recovered pool was used as a hybridisation probe to reveal those mutants in each pool that failed to be recovered from the animals and which were therefore attenuated in this animal model of infection.

In the throat colonisation model, $2\times10^8$ cells were inoculated intranasally into six C57BL/6 mice and samples taken after 48 hours. As with the skin model, bacteria containing a transposon Tn917 insertion within a virulence gene failed to be recovered from mice inoculated with a mixed population of mutants, and were therefore likely to be attenuated.

Additional experiments were carried out on mutants identified through the STM screen to determine the competitive index (CI). Individual mutants were tested in mixed infections with the wild-type strain in the skin lesion model of infection (Chiang, S. L. and Mekalanos, J. J. Molecular Microbiology 1998; 27(4):797–805). As for the initial screen, groups of four CD1 mice were inoculated with equal numbers of both wild-type and mutant cells, to a total number of $1\times10^8$ cells. Bacteria recovered after 48 hours were plated out onto selective media that allows the wild-type and mutant colonies to be distinguished. The ratio of mutant bacteria to wild-type bacteria seen in the inoculum compared with the ratio in recovered bacteria is the competitive index (ratio of mutants versus wild-type in the inoculum divided by the ratio of mutants versus wild-type bacteria recovered from the animal model).

The following Examples illustrate the invention.

EXAMPLE 1

A first mutant was identified and the nucleotide sequence immediately following the transposon insertion was cloned.

The nucleotide sequence shows 100% identity at the nucleotide level to a coding sequence within the *S. pyogenes* genome, shown as SEQ ID NO. 1, with the putative protein sequence shown as SEQ ID NO. 2.

The amino acid sequence of the predicted protein product shows 43% identity to the putative NAD(P)H nitroreductase of *H. influenzae* (accession number: SW: Q57431).

Given the similarity of the putative NAD(P)H nitroreductase gene in *S. pyogenes* to the gene in *H. influenzae*, the skilled person will appreciate that similar sequences in other Streptococci and Gram-positive bacteria may also be implicated in virulence.

In the test for attenuation of virulence, the mutated microorganism was shown to be attenuated with a competitive index (CI) of 0.644.

EXAMPLE 2

A further mutant was identified and the nucleotide sequence immediately following the transposon insertion was cloned.

The nucleotide sequence has 98% identity at the nucleotide level to a sequence within the *S. pyogenes* genome, shown as SEQ ID NO. 3. The putative amino acid sequence is shown as SEQ ID NO. 4.

The amino acid sequence shows 81% identity to a probable integrase enzyme of *S. mutans* (accession number: TREMBL: 069155).

This demonstrates that the disrupted gene is at least partially identical to a probable integrase gene of *S. mutans*. However, this gene was previously unknown in *S. pyogenes*, and has not been assigned a role in virulence.

Given the similarity of the *S. pyogenes* gene to the probable integrase gene of *S. mutans*, the skilled person will appreciate that similar sequences in other Steptococci and Gram-positive bacteria may also be virulence determinants.

In the test for attenuation of virulence, the mutated microorganism was shown to be attenuated with a competitive index (CI) of 0.229.

EXAMPLE 3

A further mutant was identified and the nucleotide sequence immediately following the transposon insertion was cloned.

The nucleotide sequence has 97% identity at the nucleotide level to a sequence within the *S. pyogenes* genome, shown as SEQ ID NO. 5. The predicted amino acid sequence is shown as SEQ ID NO. 6.

The amino acid sequence shows 37% identity at the amino acid level to the GlgP protein of the unicellular cyanobacterium *Synechocystis* spp. (accession number: TREMBL: P73511).

This demonstrates that the disrupted gene is at least partially identical to the glgP gene of *Synechocystis* spp.

Given the similarity of the gene of *S. pyogenes* to the glgP gene of *Synechocystis* spp., the skilled person will appreciate that similar sequences in other Streptococci and Gram-positive bacteria may also be virulence determinants.

In the test for attenuation of virulence, the mutated microorganism was shown to be attenuated with a competitive index (CI) of 0.011.

EXAMPLE 4

A further mutant was identified and the nucleotide sequence immediately following the transposon insertion was cloned.

The nucleotide sequence has 97% identity at the nucleotide level to a sequence within the *S. pyogenes* genome, shown as SEQ ID NO. 7. The predicted amino acid sequence is shown as SEQ ID NO. 8.

The amino acid sequence shows 35% identity at the amino acid level to the BraB protein of *B. subtilis* (accession number: TREMBL: O34545).

This demonstrates that the disrupted gene is at least partially identical to the braB gene of *B. subtilis*.

Given the similarity of the braB gene of *S. pyogenes* to the braB gene in *B. subtilis*, the skilled person will appreciate that similar sequences in other Streptococci and Gram-positive bacteria may also be implicated in virulence.

In the test for attenuation of virulence, the mutated microorganism was shown to be attenuated with a competitive index (CI) of 0.88.

EXAMPLE 5

A further mutant was identified and the nucleotide sequence immediately following the transposon insertion was cloned.

The nucleotide sequence shows 99% identity at the nucleotide level to a sequence within the *S. pyogenes* genome, shown as SEQ ID NO. 9. The predicted amino acid sequence is shown as SEQ ID NO. 10.

A still further attenuated mutant was also identified with a nucleotide sequence having 98% identity at the nucleotide level to a sequence within the *S. pyogenes* genome, shown as SEQ ID NO. 11. The predicted amino acid sequence is shown as SEQ ID NO. 12.

The predicted protein of the first mutant shows 53% identity at the amino acid level to the AdcR protein of *S. pneumoniae* (accession number: TREMBL:O33703). That of the second mutant shows 79% identity at the amino acid level to the AdcC protein of *S. pneumoniae* (accession number: TREMBL: O87862).

This demonstrates that the disrupted genes are at least partially identical to the adcR and adcC genes of *S. pneumoniae*. The adcR and adcC genes are part of the adc operon (including adcR, adcC, adcB, and adcA) in *S. pneumoniae*. Therefore the attenuation of *S. pyogenes* adcR and adcC mutants could result from a failure to express the adcR and adcC genes, or the predicted downstream genes (adcB and abcA homologues). These genes have not previously been assigned a role in-virulence in *S. pyogenes*.

Given the similarity of the *S. pyogenes* genes to the adcR and adcC genes in *S. pneumoniae*, the skilled person will appreciate that similar sequences in other Steptococci and Gram-positive bacteria may be implicated in virulence.

In the test for attenuation of virulence, the mutated microorganisms were shown to be attenuated with a competitive index (CI) of 0.548 (adcR) and 0.028 (adcC).

EXAMPLE 6

A further mutant was identified and the nucleotide sequence immediately following the transposon insertion was cloned.

The nucleotide sequence has 99% identity at the nucleotide level to a sequence within the *S. pyogenes* genome, shown as SEQ ID NO. 13. The predicted amino acid sequence is shown as SEQ ID NO. 14.

The amino acid sequence shows 39% identity at the amino acid level to the DNA repair protein radC homologue (orfB) of *B. subtilis* (accession number: SW: Q02170).

This demonstrates that the disrupted gene is at least partially identical to the orfB gene of *B. subtilis*.

Given the similarity of the orfB gene of *S. pyogenes* to that of *B. subtilis*, the skilled person will appreciate that similar sequences in other Streptococci and Gram-positive bacteria may be implicated in virulence.

In the test for attenuation of virulence, the mutated microorganism was shown to be attenuated with a competitive index (CI) of 0.766.

EXAMPLE 7

A further mutant was identified and the nucleotide sequence immediately following the transposon insertion was cloned.

The nucleotide sequence has 98% identity at the nucleotide level to a sequence within the *S. pyogenes* genome, shown as SEQ ID NO. 15. The predicted amino acid sequence is shown as SEQ ID NO. 16.

The amino acid sequence shows 54% identity at the amino acid level to the biotin carboxyl carrier protein (BCCP) in *S. mutans* (accession number: SW: P29337).

This demonstrates that the disrupted gene is at least partially identical to the gene encoding BCCP of *S. mutans*. This gene was previously unknown in *S. pyogenes* and has not been assigned a role in virulence.

Given the similarity of the translated *S. pyogenes* gene to the BCCP of *S. mutans*, the skilled person will appreciate that similar sequences in other Streptococci and Gram-positive bacteria may be implicated in virulence.

In the test for attenuation of virulence, the mutated microorganisms was shown to be attenuated with a competitive index (CI) of 0.044.

EXAMPLE 8

A series of mutants were identified having sequence similarity to genes involved in citrate fermentation. The nucleotide sequences of eight mutants showed 100% identity to a sequence within the *S. pyogenes* genome, shown to SEQ ID NO. 17. The predicted amino acid sequence is shown as SEQ ID NO. 18.

The predicted protein of the *S. pyogenes* gene shows 58% identity at the amino acid level to the citF protein, citrate lyase alpha chain, of *E. coli* (accession number: SW: P75726).

The nucleotide sequences of three further mutants showed 99% identity to a different sequence within the *S. pyogenes* genome. The nucleotide sequence is shown as SEQ ID NO. 19, and the predicted amino acid sequence is shown as SEQ ID NO. 20.

The amino acid sequences show 55% identity at the amino acid level to the citE protein, citrate lyase beta chain, of *E. coli* (accession number: SW:P77770).

The nucleotide sequences of two further mutants showed 99% identity to the *S. pyogenes* nucleotide sequence identified herein as SEQ ID NO. 21. The predicted amino acid sequence is shown as SEQ ID NO. 22.

The amino acid sequences show 46% identity at the amino acid level to the CitD protein, citrate lyase acyl carrier protein (citrate lyase gamma chain), of *E. coli* (accession number: SW: P77618).

Two further mutants were identified with nucleotide sequences which showed 99% identity to a nucleotide sequence from *S. pyogenes*, identified herein as SEQ ID NO. 23. The predicted amino acid sequence as SEQ ID NO. 24.

The amino acid sequences show 34% identity at the amino acid level to the CitC protein, citrate (pro-3s)-lyase (ligase), of *E. coli* (accession number: SW: P77390).

A further mutant was identified with a nucleotide sequence having 99% sequence identity to the *S. pyogenes* nucleotide sequence identified herein as SEQ ID NO. 25. The predicted amino acid sequence is shown as SEQ ID NO. 26.

The amino acid sequence shows 37% identity at the amino acid level to the CitX protein, of *E. coli* (accession number: SW: P77563).

A further three mutants were identified with nucleotide sequences showing 100% identity to the *S. pyogenes* nucleotide sequence identified herein as SEQ ID NO. 27. The predicted amino acid sequence is shown as SEQ ID NO. 28.

The amino acid sequences show 59% identity at the amino acid level to the OadA protein, oxaloacetate decarboxylase subunit alpha, of *K. pneumoniae* (accession number: SW:P13187).

All the predicted protein sequences of the above mutants show various degrees of identity to gene products of *E. coli* or *K. pneumoniae* required for citrate fermentation.

This demonstrates that the disrupted genes are at least partially identical to the citF, E, D, C, X and oadA genes of *E. coli* or *K. pneumoniae*. The genes involved in citrate fermentation are located together at a single locus on the chromosome in *E. coli* and *K. pneumoniae*. Therefore, the attenuation of *S. pyogenes* mutants could result from a failure to express its citFEDCX and oadA genes, or downstream genes. These genes have not previously been assigned a role in virulence.

Given the similarity of the *S. pyogenes* genes to those present in *E. coli* or *K. pneumoniae*, the skilled person will appreciate that similar sequences in other Streptococci and Gram-positive bacteria may be implicated in virulence.

Mutants for each of citF, E, D, X and oadA were tested for attenuation of virulence. The mutated microorganisms were shown to be attenuated with a competitive index (CI) of 0.122 (citF), 0.064 (citE), 0.078 (citD), 0.025 (citX) and 0.251 (oadA).

EXAMPLE 9

A further mutant was identified and the nucleotide sequence immediately following the transposon insertion was cloned.

The nucleotide sequence showed 98% identity at the nucleotide level to a sequence within the *S. pyogenes* genome, identified herein as SEQ ID NO. 29. The predicted amino acid sequence is shown as SEQ ID NO. 30.

The amino acid sequence shows 27% identity at the amino acid level to the femB protein of *S. aureas* (accession number: TREMBL: Q9X9D7).

This demonstrates that the disrupted gene is at least partially identical to the femB gene of *S. aureas*. However, this gene was previously unknown in *S. pyogenes*, and has not been assigned a role in virulence.

Given the similarity of the *S. pyogenes* gene to the femB gene in *S. aureas*, the skilled person will appreciate that similar sequences in other Steptococci and Gram-positive bacteria may be implicated in virulence.

EXAMPLE 10

A further mutant was identified and the nucleotide sequence immediately following the transposon insertion was cloned.

The nucleotide sequence has significant identity to a sequence within the S. *pyogenes* genome, shown as SEQ ID NO. 31. The predicted amino acid sequence is shown as SEQ ID NO. 32.

In the test for attenuation of virulence, the mutated microorganism was shown to be attenuated with a competitive index (CI) of 0.160.

EXAMPLE 11

A further mutant was identified and the nucleotide sequence immediately following the transposon insertion was cloned.

The nucleotide sequence has 100% identity to a sequence within the S. *pyogenes* genome, shown as SEQ ID NO. 33. The predicted amino acid sequence is shown as SEQ ID NO. 34.

EXAMPLE 12

A further mutant was identified and the nucleotide sequence immediately following the transposon insertion was cloned.

The nucleotide sequence has 98% identity at the nucleotide level to a sequence within the S. *pyogenes* genome, shown as SEQ ID NO. 35. The predicted amino acid sequence is shown as SEQ ID NO. 36.

The amino acid sequence shows 46% identity at the amino acid level to the subtilin transport ATP-binding protein of *Bacillus subtilis* (accession number: SW: P33116).

This demonstrates that the disrupted gene is at least partially identical to the braB gene of *B. subtilis*.

Given the similarity of the gene of S. *pyogenes* to that in *B. subtilis*, the skilled person will appreciate that similar sequences in other Streptococci and Gram-positive bacteria may be implicated in virulence.

In the test for attenuation of virulence, the mutated microorganism was shown to be attenuated with a competitive index (CI) of 0.128.

EXAMPLE 13

A further mutant was identified and the nucleotide sequence immediately following the transposon insertion was cloned.

The nucleotide sequence has 98% identity to a sequence within the S. *pyogenes* genome, shown as SEQ ID NO. 37. The predicted amino acid sequence is shown as SEQ ID NO. 38.

EXAMPLE 14

A further mutant was identified and the nucleotide sequence immediately following the transposon insertion was cloned.

The nucleotide sequence has 98% identity to a sequence within the S. *pyogenes* genome, shown as SEQ ID NO. 39. The predicted amino acid sequence is shown as SEQ ID NO. 40.

The amino acid sequence shows 29% identity at the amino acid level to a 36.9 kDa hypothetical protein from *E. coli* (accession number SW: P33019).

This demonstrates that the disrupted gene is at least partially identical to the gene of *E. coli*. Other similar sequences may be implicated in virulence.

In the test for attenuation of virulence, the mutated microorganism was shown to be attenuated with a competitive index (CI) of 0.747.

EXAMPLE 15

A further mutant was identified and the nucleotide sequence immediately following the transposon insertion was cloned.

The nucleotide sequence has 99% identity to a sequence within the S. *pyogenes* genome, shown as SEQ ID NO. 41. The predicted amino acid sequence is shown as SEQ ID NO. 42.

The amino acid sequence shows 29% identity at the amino acid level to a 89 kDa hypothetical protein from *A. fulgidus* (accession number TREMBL: 028455).

This demonstrates that the disrupted gene is at least partially identical to the gene of *E. coli*. Other, similar sequences may be implicated in virulence.

In the test for attenuation of virulence, the mutated microorganism was shown to be attenuated with a competitive index (CI) of 0.588.

EXAMPLE 16

A further mutant was identified and the nucleotide sequence immediately following the transposon insertion was cloned.

The nucleotide sequence has 99% identity to a sequence within the S. *pyogenes* genome, shown as SEQ ID NO. 43. The predicted amino acid sequence is shown as SEQ ID NO. 44.

EXAMPLE 17

A further mutant was identified and the nucleotide sequence immediately following the transposon insertion was cloned.

The nucleotide sequence has 98% identity to a sequence within the S. *pyogenes* genome, shown as SEQ ID NO. 45. The predicted amino acid sequence is shown as SEQ ID NO. 46.

EXAMPLE 18

A further mutant was identified and the nucleotide sequence immediately following the transposon insertion was cloned.

The nucleotide sequence has 97% identity to a sequence within the S. *pyogenes* genome, shown as SEQ ID NO. 47. The predicted amino acid sequence is shown as SEQ ID NO. 48.

EXAMPLE 19

A further mutant was identified and the nucleotide sequence immediately following the transposon insertion was cloned.

The nucleotide sequence has 98% identity at the nucleotide level to a sequence within the S. *pyogenes* genome, shown as SEQ ID NO. 49. The predicted amino acid sequence is shown as SEQ ID NO. 50.

The amino acid sequence shows 47% identity at the amino acid level to the ciaH protein of S. *pneumoniae* (accession number: SW: Q54955).

This demonstrates that the disrupted gene is at least partially identical to the ciaH gene of *S. pneumoniae*.

Given the similarity of the ciaH gene of *S. pyogenes* to the ciaH gene of *S. pneumoniae*., the skilled person will appreciate that similar sequences in other Streptococci and Gram-positive bacteria may be implicated in virulence.

In the test for attenuation of virulence, the mutated microorganism was shown to be attenuated with a competitive index (CI) of 0.205.

EXAMPLE 20

A further mutant was identified and the nucleotide sequence immediately following the transposon insertion was cloned.

The nucleotide sequence has 98% identity at the nucleotide level to a sequence within the *S. pyogenes* genome, shown as SEQ ID NO. 51. The predicted amino acid sequence is shown as SEQ ID NO. 52.

The amino acid sequence shows 39% identity at the amino acid level to the mucA homologue protein of *S. pneumonia* (accession number: TREMBL: Q9ZBB1).

This demonstrates that the disrupted gene is at least partially identical to the mucA gene of *S. pneumoniae*.

Given the similarity of the gene of *S. pyogenes* to the mucA gene of *S. pneumoniae*, the skilled person will appreciate that similar sequences in other Streptococci and Gram-positive bacteria may be implicated in virulence.

In the test for attenuation of virulence, the mutated microorganism was shown to be attenuated with a competitive index (CI) of 0.547.

EXAMPLE 21

A further mutant was identified and the nucleotide sequence immediately following the transposon insertion was cloned.

The nucleotide sequence has 98% identity at the nucleotide level to a sequence within the *S. pyogenes* genome, shown as SEQ ID NO. 53. The predicted amino acid sequence is shown as SEQ ID NO. 54.

The amino acid sequence shows 69% identity at the amino acid level to the gidA protein of *B. subtilis* (accession number: SW:P39815).

This demonstrates that the disrupted gene is at least partially identical to the gene of *B. subtilis*.

Given the similarity of the *S. pyogenes* to the gidA gene of *B. subtilis*, the skilled person will appreciate that similar sequences in other Streptococci and Gram-positive bacteria may be implicated in virulence.

In the test for attenuation of virulence, the mutated microorganism was shown to be attenuated with a competitive index (CI) of 0.444.

EXAMPLE 22

A further mutant was identified and the nucleotide sequence immediately following the transposon insertion was cloned.

The nucleotide sequence has 98% identity at the nucleotide level to a sequence within the *S. pyogenes* genome, shown as SEQ ID NO. 55. The predicted amino acid sequence is shown as SEQ ID NO. 56.

The amino acid sequence shows 74% identity at the amino acid level to the dltA protein of *S. mutans* (accession number: SW:Q53526).

This demonstrates that the disrupted gene is at least partially identical to the dltA gene of *S. mutans*.

Given the similarity of the *S. pyogenes* gene to the dltA gene of *S. mutans*, the skilled person will appreciate that similar sequences in other Gram-positive bacteria may be implicated in virulence.

In the test for attenuation of virulence, the mutated microorganism was shown to be attenuated with a competitive index (CI) of 0.205.

EXAMPLE 23

A further mutant was identified and the nucleotide sequence immediately following the transposon insertion was cloned.

The nucleotide sequence has 98% identity at the nucleotide level to a sequence within the *S. pyogenes* genome, shown as SEQ ID NO. 57. The predicted amino acid sequence is shown as SEQ ID NO. 58.

The amino acid sequence shows 41% identity at the amino acid level to the hmgA protein of *A. fulgidus* (accession number: SW: 028538).

This demonstrates that the disrupted gene is at least partially identical to the gene of *A. fulgidus*.

Given the similarity of the gene of *S. pyogenes* to the hmgA gene of *A. fulgidus*, the skilled person will appreciate that similar sequences in other Streptococci and Gram-positive bacteria may be implicated in virulence.

In the test for attenuation of virulence, the mutated microorganism was shown to be attenuated with a competitive index (CI) of 0.205.

EXAMPLE 24

A first mutant was identified and the nucleotide sequence immediately following the transposon insertion was cloned.

The nucleotide sequence has 99% identity to a sequence within the *S. pyogenes* genome, shown as SEQ ID NO. 59. The predicted amino acid sequence is shown as SEQ ID NO. 60.

The amino acid sequence shows 34% identity at the amino acid level to the putative JAG protein from *T. maritima* (accession number TREMBL: Q9X1H1).

This demonstrates that the disrupted gene from *S. pyogenes* is at least partially identical to the gene of *T. maritima*. Similar sequences in other Gram-negative bacteria may be implicated in virulence.

EXAMPLE 25

A further mutant was identified and the nucleotide sequence immediately following the transposon insertion was cloned.

The nucleotide sequence has 99% identity to a sequence within the *S. pyogenes* genome, shown as SEQ ID NO. 61. The predicted amino acid sequence is shown as SEQ ID NO. 62.

The amino acid sequence shows 49% identity at the amino acid level to a 49.4 kDa hypothetical protein from *S. suis* (accession number TREMBL: Q9X4U3).

This demonstrates that the disrupted gene of *S. pyogenes* is at least partially identical to the gene of *S. suis*. Similar sequences in other Gram-negative bacteria may also be implicated in virulence.

What is claimed is:

1. A screening assay for the identification of an antimicrobial drug, comprising:
   (i) contacting a citrate lyase acyl carrier protein (citD) with a potential drug, wherein the citD protein comprises the amino acid sequence of SEQ ID NO:22; and
   (ii) determining whether the potential drug inhibits citD protein activity, wherein inhibition of citD protein activity is indicative of an antimicrobial drug.

* * * * *